United States Patent [19]

Almond et al.

[11] Patent Number: 4,694,071

[45] Date of Patent: Sep. 15, 1987

[54] POLYPEPTIDES USEFUL IN VACCINATION AGAINST ENTEROVIRUSES

[75] Inventors: Jeffrey W. Almond, Leicester; Phillip D. Minor, London; David M. A. Evans, Tring; Geoffrey C. Schild, London, all of United Kingdom

[73] Assignee: National Research Development Corporation, London, England

[21] Appl. No.: 619,155

[22] PCT Filed: Oct. 11, 1983

[86] PCT No.: PCT/GB83/00254

§ 371 Date: Jun. 8, 1984

§ 102(e) Date: Jun. 8, 1984

[87] PCT Pub. No.: WO84/01575

PCT Pub. Date: Apr. 26, 1984

[30] Foreign Application Priority Data

Oct. 11, 1982 [GB] United Kingdom ................. 8228976
Jun. 24, 1983 [GB] United Kingdom ................. 8317242

[51] Int. Cl.[4] .......................... C07K 7/06; C07K 7/08; A61K 39/02

[52] U.S. Cl. .................................... 530/329; 530/326; 530/403; 424/88

[58] Field of Search ....................... 530/329, 326, 403; 424/88

[56] References Cited

U.S. PATENT DOCUMENTS 4,554,101 11/1985 Hopp .................................. 530/329

FOREIGN PATENT DOCUMENTS 0044710 1/1982 European Pat. Off. .
0065924 12/1982 European Pat. Off. .
0068719 1/1983 European Pat. Off. .
0076489 4/1983 European Pat. Off. .
0110791 6/1984 European Pat. Off. .
WO82/03632 10/1982 PCT Int'l Appl. .
WO83/03547 10/1983 PCT Int'l Appl. .
WO83/03972 11/1983 PCT Int'l Appl. .
2108510 5/1983 United Kingdom .

OTHER PUBLICATIONS

"Poliomyelitis–Epidemiology, Molecular Biology and Immunology", P. D. Minor et al., Nature, vol. 299, Sep. 9, 1982, pp. 109–110.
"Primary Structure, Gene Organization and Polypeptide Expression of Poliovirus RNA", Kitamura et al., Nature, vol. 291, Jun. 18, 1981, pp. 547–553.
"Complete Nucleotide Sequence of the Attenuated Poliovirus Sabin I Strain Genome", A. Nomoto et al, Proc. Natl. Acad. Sci., USA, vol. 79, Oct. 1982, pp. 5793–5797.
"Location and Primary Structure of a Major Antigenic Site for Poliovirus Neutralisation", P. D. Minor et al, Nature, vol. 301, Feb. 24, 1983, pp. 674–679.
"Poliovirus Type 3–Molecular Cloning of the Genome and Nucleotide Sequence of the Region Encoding the Protease and Polymerase Proteins", A. J. Cann et al, Nuc. Acid Res., vol. 11, No. 5, 1983, pp. 1267–1281.
"Functional Basis of Poliovirus Neutralization Determined with Monospecific Neutralising Antibodies", E. A. Emini et al., J. Virology, vol. 46, No. 2, May 1983, pp. 466–475.
"Critical Role of an Eight–Amino Acid Sequence of VP1 in Neutralisation of Poliovirus Type 3", D. M. A. Evans et al., Nature, vol. 304, Aug. 4, 1983, pp. 459–462.
"Priming for and Induction of Antipoliovirus Neutralising Antibodies by Synthetic Peptides", E. A. Emini et al, Nature, vol. 304, Aug. 25, 1983, pp. 699–703.
"Will Peptides Makes Vaccines", P. Newmask, Nature, vol. 304, Sep. 1, 1983.
"Neutralizing Site of Poliovirus" F. Brown, Nature, vol. 304, Aug. 4, 1983, pp. 395–396.

*Primary Examiner*—Delbert R. Phillips
*Attorney, Agent, or Firm*—Oblon, Fisher, Spivak, McClelland & Maier

[57] ABSTRACT

A synthetic polypeptide, suitable for use in vaccination against or diagnosis of a disease caused by an enterovirus, is an octapeptide coded for by codons 93–100 in the RNA sequence coded for the structural capsid protein VP1 for poliovirus type 3 Sabin strain or by equivalent codons of another enterovirus or is an antigenic equivalent of such an octapeptide, the numbers of the codons being counted from the 5'-terminus of the nucleotide sequence for the VP1 capsid protein.

29 Claims, 1 Drawing Figure

| | | | | | | | | | | | |
|---|---|---|---|---|---|---|---|---|---|---|---|
| GGU* | AUU | GAA | GAU | UUG | AUU | UCU | GAA | GUU | GCA | CAG | GGC |
| GCC | CUA | ACU | UUG | UCA | CUC | CCG | AAG | CAA | CAG | GAU | AGC |
| UUA | CCU | GAU | ACU | AAG | GCC | AGU | GGC | CCG | GCG | CAU | UCC |
| AAG | GAG | GUA | CCU | GCA | CUC | ACU | GCA | GUC | GAG | ACU | GGA |
| GCC | ACC | AAU | CCU | CUG | GCA | CCA | UCC | GAC | ACA | GUU | CAA |
| ACG | CGC | CAC | GUA | GUC | CAA | CGA | CGC | AGC | AGG | UCA | GAG |
| UCC | ACA | AUA | GAA | UCA | UUC | UUC | GCA | CGC | GGG | GCG | UGC |
| GUC | GCU | AUU | AUU | GAG | GUG | GAC | AAU | GAA | CAA | CCA | ACC |
| ACC | CGG | GCA | CAG | AAA | CUA | UUU | GCC | AUG | UGG | CGC | AUU |
| ACA | UAC | AAA | GAU | ACA | GUG | CAG | UUG | CGC | CGU | AAG | UUG |
| GAG | UUU | UUC | ACA | UAC | UCU | CGU | UUU | GAC | AUG | GAA | UUC |
| ACC | UUC | GUG | GUA | ACC | GCC | AAC | UUC | ACC | AAC | GCU | AAU |
| AAU | GGG | CAU | GCA | CUC | AAC | CAG | GUG | UAC | CAG | AUA | AUG |
| UAC | AUC | CCC | CCA | GGG | GCA | CCC | ACA | CCA | AAG | UCA | UGG |
| GAC | GAC | UAC | ACU | UGG | CAA | ACA | UCU | UCC | AAC | CCG | UCC |
| AUA | UUU | UAC | ACC | UAU | GGG | GCU | GCC | CCG | GCG | CGA | AUC |
| UCA | GUG | CCA | UAC | GUG | GGG | UUA | GCC | AAU | GCU | UAC | UCG |
| CAC | UUU | UAC | GAC | GGC | UUC | GCC | AAG | GUG | CCA | UUG | AAG |
| ACA | GAU | GCC | AAU | GAC | CAG | AUU | GGU | GAU | UCC | UUG | UAC |
| AGC | GCC | AUG | ACA | GUU | GAU | GAC | UUU | GGU | GUA | UUG | GCA |
| GUU | CGU | GUU | GUC | AAU | GAU | CAC | AAC | CCC | ACU | AAA | GUA |
| ACC | UCC | AAA | GUC | CGC | AUU | UAC | AUG | AAA | CCC | AAA | CAC |
| GUA | CGU | GUC | UGG | UGC | CCU | AGA | CCG | CCG | CGC | GCG | GUA |
| CCU | UAU | UAU | GGA | CCA | GGG | GUG | GAC | UAU | AAG | AAC | AAC |
| UUG | GAC | CCC | UUA | UCU | GAG | AAA | GGU | UUG | ACC | ACA | UAU |

* no 1

POLYPEPTIDES USEFUL IN VACCINATION AGAINST ENTEROVIRUSES

TECHNICAL FIELD

This invention relates to polypeptides having biological activity, particularly for use in vaccines for diseases caused by enteroviruses in particular polioviruses.

BACKGROUND ART

In the past, vaccines for diseases caused by enteroviruses have relied either on inactivated virus or on live attenuated virus. This can be illustrated by reference to the history or vaccines against poliomyelitis which began in the 1950's with the Salk vaccine, prepared by growing poliovirus in tissue culture, inactivating it with formaldehyde. The resulting inactivated or dead virus is administered by injection and appears to stimulate circulating antibodies which can neutralise the virus. A so-called trivalent vaccine is generally injected containing inactivated polio-viruses of types 1, 2 and 3 in order to immunise against all of these. Apart from the expense of preparing this vaccine, it also has the disadvantage that it is typically made using a potentially virulent virus and there is a delicate margin between rendering the virus non-infectious while at the same time retaining its immunogenicity. In fortunately rare cases, the vaccine virus can actually cause polio.

An alternative vaccine was subsequently developed, the Sabin vaccine, which was prepared by passage of the virus in cell cultures until it lost its ability to cause the disease, i.e. it became attenuated. This live attenuated virus is administered orally and replicates in the gut to induce a protective antibody response. This vaccine also has the disadvantage of being expensive since each batch of the vaccine has to be extensively tested in animals. In addition, there are three major disadvantages stemming from the use of a live virus in the vaccine. Firstly, the vaccine viruses can, very occasionally, revert to virulence causing paralysis in the patient and his contacts. Type 3 polioviruses are most troublesome in this respect being the least stable of the three types. Secondly, although the Sabin vaccine is widely used in developed countries, it does not apparently work in tropical countries, either because the virus does not replicate under those climatic conditions producing no immune response, or because the virus actually administered is no longer live. Finally, while live viruses are being used in vaccines in this way, it will never be possible to eradicate the poliovirus entirely.

There has therefore been a requirement for a vaccine which is simply and inexpensively produced, does not employ whole viruses and, while inducing an appropriate immune response, does not risk producing the corresponding disease.

Although the live-attenuated poliovirus vaccines developed by Sabin have been in use for more than twenty years, the molecular basis of their reduced neuropatho genicity remains unclear. Numerous studies, comparing the vaccine strains with their neurovirulent progenitors, have been made. Recently, Nomoto et al determined the RNA sequence of the attenuated poliovirus type 1 Sabin strain (Proc. Natn. Acad. Sci USA 79 5793–5797 (1982)) and compared their sequence with that obtained by Kitamura et al for the poliovirus type 1 Mahoney strain (see Nature (1981) 291 547–553). They were able to identify base substitutions particularly in the region coding for the VP1 capsid protein and suggested that base substitutions in this coding region might contribute to the attenuation of the virus i.e. that changes in this region would render the virus nonvirulent but still capable of producing an equivalent immune response. This supposition is not supported by any experimental results.

The role of VP1 in poliovirus antigenicity has also been discussed by Minor et al in Nature (1982) 299 109–110 where it was reported that the isolated whole polypeptides VP1, VP2 and VP3 were only capable of inducing low levels of neutralizing antibody in animals. Experimental results indicated that the antigenic determinants were likely to be complex, being specified by the tertiary configuration of polypeptide(s) rather than a simple amino acid sequence.

DISCLOSURE OF THE INVENTION

The present invention stems from identification of an antigenically significant polypeptide coded for by an RNA sequence within the genome region coding for the structural capsid protein VP1 of an enterovirus.

The present invention provides a synthetic polypeptide, suitable for use in vaccination against or diagnosis of a disease caused by an enterovirus, which is a hexapeptide coded for by codons 93 to 98, preferably an octapeptide coded for by codons 93 to 100, in the RNA sequence coding for the structural capsid protein VP1 of a poliovirus type 3 Sabin strain or by equivalent codons of another enterovirus or is an antigenic equivalent of such a hexapeptide or octapeptide, the numbers of the codons being counted from the 5'-terminus of the nucleotide sequence coding for the VP1 capsid protein.

The polypeptides of the invention are synthetic polypeptides. They comprise an antigenically effective hexapeptide unit, preferably, octapeptide unit coded for as defined above. The polypeptides are not naturally-occurring polypeptides, such as the VP1 capsid protein itself, which have been recovered in a suitably pure form. In other words, the hand of man has been involved in the making of the polypeptides of the invention. A polypeptide of the invention may be obtained by effecting degradation of a naturally-occurring polypeptide, for example by enzymic digestion of a VP1 capsid protein; by chemical synthesis of the polypeptide from single amino acids or smaller preformed peptides; or by employing the methods of genetic engineering to produce an organism which makes the polypeptide in recoverable form.

By "equivalent codons" is meant a sequence of eight codons in the RNA sequence coding for the structural capsid protein VP1 of another enterovirus corresponding to the codon sequence 93 to 98 in the RNA sequence coding for the structural capsid protein VP1 of the poliovirus type 3 Sabin strain. The "equivalent codons" are therefore the counterpart eight codons in the RNA sequence coding for the structural capsid protein VP1 of the other enterovirus to codons 93 to 98 for the poliovirus type 3 Sabin strain. This can readily be determined by lining up the base sequence in the RNA sequence of the other enterovirus coding for the VP1 protein with the corresponding base sequence of the poliovirus type 3 Sabin strain. While it is possible that the "equivalent codons" in the other enterovirus may also be Nos. 93 to 98 counting from the 5' terminus, this is not necessarily the case. In the poliovirus type 3 Leon strain, which is the virulent progenitor of the attenuated Sabin strain, the equivalent codons are Nos. 93 to 98 counting from the 5' terminus. However, in the poliovirus type 1 strains Sabin and Mahoney the equivalent codons are Nos. 95 to 100 counting from the 5' terminus.

An "antigenic equivalent" of any particular "natural" polypeptide sequence coded for by an existing enterovirus (whether wild-type or mutant) is a polypeptide which, if not itself immunogenic, when linked to material which renders it immunogenic is capable of inducing the same or very similar antibody response as the "natural" polypeptide, i.e. the antibody produced, though possibly not precisely identical, would neutralise the same strain and type of enterovirus and hence antigenicity is effectively equivalent.

An antigenic equivalent of a "natural" polypeptide sequence may be an hexapeptide or octapeptide which, however, is not coded for by a wild-type or known mutant enterovirus, but includes one or more changes to the amino acids in the sequence which do not affect the antigenicity. Thus, one or more amino acids of a "natural" hexapeptide or octapeptide sequence may be replaced by, respectively, one or more other amino acids which preserve the physicochemical character of the original, i.e. in terms of charge density, hydrophilicity/hydrophobicity, size and configuration, and hence preserve the immunological structure. For example, Ser may be replaced by Thr and vice versa, Glu may be replaced by Asp and vice versa and Gln may be replaced by Asn and vice versa.

An antigenic equivalent may also be a longer polypeptide which comprises a "natural" hexapeptide or octapeptide sequence but still has equivalent antigenicity. The "natural" hexapeptide or octapeptide sequence will thus be exposed in the longer polypeptide so as to be available to induce the appropriate immune response and not "buried" in the interior of the longer polypeptide and consequently unable itself to provoke an immune response.

Yet further antigenic equivalents may be formed by modifying reactive groups within a natural sequence or modifying the N-terminal amino and/or C-terminal carboxyl group. Such equivalents can include salts formed with acids and/or bases, particularly physiologically acceptable inorganic and organic acids and bases. Other equivalents may include modified carboxyl groups to produce esters or amides or may include typical amino acid protecting groups such as N-t-butoxycarbonyl. Preferred modifications of this type are those which enable the production of a more stable, active polypeptide which will be less prone to enzymic breakdown in vivo.

A combination of two or three of the types of variations of a "natural" sequence described above may be used to arrive at an antigenic equivalent polypeptide of the invention. It has not yet been unequivocally established whether the nucleotide sequence coding for the VP1 capsid protein of poliovirus type 3 Sabin strain actually commences with the codons GGU AUU . . . as shown in the FIGURE of the accompanying drawing or with the codon GGC . . . which is the twelfth codon in the FIGURE. Nevertheless, herein the codons for the nucleotide sequence of the VP1 capsid protein of poliovirus type 3 Sabin strain are counted from the first codon in the Figure, GGU.

The present invention will now be described with particular reference to the polypeptides coded for by polioviruses, though it will be appreciated that the concept of the invention is considered to apply equally well to other enteroviruses, i.e. viruses which are found in the intestine, e.g. ECHO (enteric cytopathic human orphan) and Coxsackie B viruses. In accordance with convention, the bases referred to herein are as follows:

A = adenine
G = guanine
C = cytosine
U = uracil

Similarly, in accordance with convention, the following abbrevations are used for the amino acid radicals:

Alanine = Ala
Arginine = Arg
Asparagine = Asn
Aspartic acid = Asp
Cysteine = Cys
Glutamine = Gln
Glutamic acid = Glu
Glycine = Gly
Histidine = His
Isoleucine = Ile
Leucine = Leu
Lysine = Lys
Methionine = Met
Phenylalanine = Phe
Proline = Pro
Serine = Ser
Threonine = Thr
Tryptophan = Trp
Valine = Val (Wherever these amino acids are mentioned they cover both the D- and L- configuration, though it is preferred, in accordance with the present invention, that the amino acids should take the natural, i.e. the L-, configuration)

In accordance with these above notations, the appropriate RNA sequence and corresponding octapeptide coded for by the Sabin type 3 poliovirus is as follows:

```
93                                    100
GAA CAA CCA ACC ACC CGG GCA CAG
H—Glu—Gln—Pro—Thr—Thr—Arg—Ala—Gln—OH
```

This octapeptide and longer polypeptides incorporating this octapeptide sequence which are antigenic equivalents thereof are preferred polypeptides of the invention.

As previously indicated, the polypeptide of the invention need not conform precisely to that coded for by a known enterovirus; changes in bases which lead to changes in amino acids having no effect on the antigenic activity of the polypeptide are permissible. The following Table 1 indicates in the first column the type 3 Sabin poliovirus polypeptide identified above, in the second and third columns the polypeptide of the type 1 Sabin and Mahoney polioviruses respectively, and in the remaining columns the polypeptide of mutants of the type 3 Sabin poliovirus.

The blanks in Table 1 indicate that the amino acid is unchanged from that indicated for the type 3 Sabin poliovirus. It should be noted that, whereas the RNA sequence coding for the type 3 Sabin poliovirus is from codons 86 to 103 counting from the 5'-terminus of the VP1 genome, the RNA sequence coding for the Type 1 Sabin and Mahoney polypeptides is from codons 88 to 105 counting from the 5'-terminus of the VP1 genome . . .

The important region of the polypeptide in the Sabin poliovirus Type 3 is that coded for by codons 93 to 100 and, in other enteroviruses, the polypeptide coded for by the equivalent codons. A preferred polypeptide, suitable for use as a vaccine for or in the diagnosis of type 3 poliovirus, is the octapeptide of formula (I):

$$H-A-A_1-A_2-A_3-A_4-A_5-A_6-A_7-OH \quad (I)$$

in which $A_0$ is Glu, $A_4$ is Thr or Ser and $A_5$ is Arg. By reference to Table 1, a polypeptide of the invention may be one of formula (I) wherein (A) $A_o$ is Glu, $A_1$ is Gln, $A_2$ is Pro, $A_3$ is Thr, $A_4$ is Thr, $A_5$ is Arg, $A_6$ is Ala and $A_7$ is Gln, or (B), with the others of $A_o$ to $A_7$ being as defined in (A),
- (a) $A_o$ is Gly, or
- (b) $A_3$ is Ile, Ala or Asn, or
- (c) $A_4$ is Asn, Ser or Ile, or
- (d) $A_5$ is Gln or Trp, or
- (e) $A_6$ is Thr or Val, or
- (f) $A_7$ is Leu, Pro, Arg or His; or further
- (g) $A_5$ is Gly, or
- (h) $A_3$ is Ser, Ile or Asn and $A_6$ is Thr, or
- (i) $A_3$ is Ile, $A_4$ is Asn or Ala and $A_6$ is Thr; or an antigenic equivalent thereof.

A preferred polypeptide, suitable for use as a vaccine for or in the diagnosis of type 1 poliovirus, is the polypeptide of formula (I) in which: $A_1$ is Ala, $A_2$ is Ser, $A_3$ is Thr, $A_5$ is Asn, $A_6$ is Lys, $A_7$ is Asp and either (A) $A_o$ is Ser and $A_4$ is Lys or (B) $A_o$ is Pro and $A_4$ is Thr; or an antigenic equivalent thereof.

The present invention also includes polypeptides of more than eight amino acid polypeptide. Further amino acids and/or peptides can be linked to one or both ends of the eight amino acid polypeptide chain, for example to build up an eighteen amino acid polypeptide. Alternatively, the present eight amino acid polypeptide sequences themselves or longer polypeptides containing these sequences may be linked at one or both ends to a protein and/or some other carrier.

When for example an eight amino acid sequence of a "natural" octapeptide or of an octapeptide antigenic equivalent thereof is included in a longer polypeptide, the additional amino acids attached to the eight amino acid polypeptide preferably correspond with the amino acids linked to the "natural" polypeptide in the corresponding natural VP1 capsid protein. In the Type 3 Sabin poliovirus, the first N-terminal amino acid which may be added to the eighteen amino acid sequence is Asn (coded for by AAU as can be seen from the Figure of the accompanying drawing) and the first C-terminus amino acid which may be added in this instance is Lys (coded for by AAA). Appropriate further amino acids in this case can be determined from the Figure.

The present eight amino acid sequence can therefore be built up into the eighteen amino acid polypeptide which is coded for by codons 86 to 103 in the RNA sequence coding for the structural capsid protein VP1 of a poliovirus type 3 Sabin strain or by equivalent codons of another enterovirus, or an antigenic equivalent of such a polypeptide. Such an octadecapeptide can be represented by the formula (II):

$$H-A_{-7}-A_{-6}-A_{-5}-A_{-4}-A_{-3}-A_{-2}-A_{-1}-A_0-A_1-A_2-A_3-A_4-A_5-A_6-A_7-A_8-A_9-A_{10}-OH \quad (II)$$

An octadecapetide suitable for use as a vaccine for type 3 poliovirus is one of formula (II) in which:

$A_{-7}$ is Ala,
$A_{-6}$ is Ile,
$A_{-5}$ is Ile,
$A_{-4}$ is Glu,
$A_{-3}$ is Val,
$A_{-2}$ is Asp,
$A_{-1}$ is Asn,
$A_0$ to $A_7$ are as defined above in relation to a polypeptide of formula (I) for a vaccine for type 3 poliovirus,
$A_8$ is Lys,
$A_9$ is Leu and
$A_{10}$ is Phe; or an antigenic equivalent thereof.

An octadecapeptide suitable for use as a vaccine for type 1 poliovirus is one of formula (II) in which:

$A_{-4}$ is Thr,
$A_{-3}$ is Val,
$A_{-2}$ is Asp,
$A_{-1}$ is Asn,
$A_1$ to $A_3$ and $A_5$ to $A_7$ are as defined above in relation to a polypeptide of formula (I) for a vaccine for type 1 poliovirus,
$A_8$ is Lys,
$A_9$ is Leu,
$A_{10}$ is Phe, and either (A) $A_{-7}$ is Ala, $A_{-6}$ is Ile, $A_{-5}$ is Ile, $A_o$ is Ser and $A_4$ is Lys or (B) $A_{-7}$ is Thr, $A_{-6}$ is Thr, $A_{-5}$ is Met, $A_o$ is Pro and $A_4$ is Thr; or an antigenic equivalent thereof.

A preferred hexapeptide, suitable for use as a vaccine for type 3 poliovirus, has the formula (IIa)

$$H-A_0-A_1-A_2-A_3-A_4-A_5-OH \quad (IIa)$$

in which (A) $A_o$ is Glu, $A_1$ is Gln, $A_2$ is Pro, $A_3$ is Thr, $A_4$ is Thr or $A_5$ is Arg or (B), with the remainder of $A_o$ to $A_5$ being as defined in (A), (a) $A_o$ is Gly, or (b) $A_3$ is Ile, Ser, Ala or Asn, or (c) $A_4$ is Asn, Ser or Ile, or (d) $A_5$ is Gln, Trp or Gly, or (e) $A_3$ is Ile and $A_4$ is Asn or Ala.

A preferred hexapeptide, suitable for use as a vaccine for type 1 poliovirus, has the formula (IIa) in which $A_1$ is Ala, $A_2$ is Ser, $A_3$ is Thr, $A_5$ is Asn and either (A) $A_o$ is Ser and $A_4$ is Lys or (B) $A_o$ is Pro and $A_4$ is Thr.

In accordance with what has been stated above, the present invention also covers the intermediate polypeptide chains of 7 to 17 amino acids between a "natural" hexapeptide or a hexapeptide antigenic equivalent thereof and an octadecapeptide as broadly defined above, for example between the hexapeptide (IIa) or octapeptide (I) and the octadecapeptide (II), i.e. each including the eight amino acid sequence but being built on sequentially at either or both ends of the chain.

Larger compounds are such that the hexa- and particularly the octapeptide is positioned so as to be readily available to induce the appropriate immune response and in particular, so that it is not "buried" in the interior of a molecule. Thus, for example, repeats of polypeptide may be linked together by either non-covalent or, preferably, covalent bonds. Where no appropriate amino acid is contained in the polypeptide sequence of the present invention, additional acids can be attached at either terminus for this purpose, in particular Cys which will enable covalent bonding through the formation of a disulphide linkage.

Alternatively, a longer polypeptide including the polypeptide of the invention may be formed into a loop by including groups which can link together at each terminus of the chain. A loop can of course be created by formation of an amide link between the N-terminus and C-terminus which can occur irrespective of the amino acids at those termini.

A synthetic polypeptide of the present invention, if not itself immunogenically active, may be linked to a carrier in order to create a conjugate which will be immunogenically active. The carrier in that case may be a protein such as bovine serum albumin, thyroglobulin, ovalbumin or keyhole limpet hemocyanin, or palmitic acid. For immunization of humans, the carrier must be a physiologically acceptable carrier acceptable to humans and safe. Preferably however, the polypeptide is linked to tetanus toxoid and/or diphtheria toxoid thus providing both an immunogen and a multivalent vaccine at the same time. Alternatively the polypeptide may be chemically bonded to inert carriers where they can be used to assay and/or isolate by affinity chromatography antibodies to the appropriate virus. Examples of such inert carriers are dextrans e.g. sepharose.

The present invention also provides a process for the preparation of a synthetic polypeptide of the invention, which process comprises identifying either (a) the codons in the RNA sequence coding for the structural capsid protein VP1 of an enterovirus which are or which are equivalent to codons 93 to 98 for a poliovirus type 3 Sabin strain or (b) the corresponding codons in a DNA sequence corresponding to said RNA sequence; and producing a polypeptide comprising the hexapeptide sequence corresponding to the codons thus identified or an antigenic equivalent thereof.

A synthetic polypeptide of the present invention which is coded for by codons in the RNA sequence coding for the structural capsid protein VP1 of an enterovirus may be obtained by the degradation of a viral capsid protein VP1 from an enterovirus, for example by successive enzymic digestion. However, it is more convenient to prepare these polypeptides by chemical synthesis, for example by one of the generally known methods. In these methods, the polypeptide is usually built up either from N-terminus or, more usually, the C-terminus using either single amino acids or preformed peptides containing two or more amino acid residues. Particular techniques for synthesising polypeptides include the classical methods where the polypeptides of increasing size are usually isolated before each amino acid or preformed peptide addition. Alternatively, solid phase peptide synthesis may be employed where the peptide is built up attached usually to a resin e.g. a Merrifield resin. In these syntheses, groups on the amino acids will generally be in protected form using standard protecting groups such as t-butoxycarbonyl as mentioned previously. If necessary, these protecting groups are conveniently cleaved once the synthesis is complete, though they may be retained where they do not affect the ability of the compound including the polypeptide to provoke an appropriate immune response. Other modifications of the polypeptide may either be introduced during the synthesis or at the end of it.

A still further possible method for producing the polypeptides of the invention is by employing the techniques of genetic engineering whereby a DNA or RNA sequence coding for the polypeptide is introduced into the plasmid which itself is introduced into an organism e.g. a bacterium, which can be induced to make the polypeptide in recoverable form. The present invention thus not only covers the polypeptide, but also a DNA or RNA sequence coding for the polypeptide which can be used in such a synthesis. However, in view of the small number of amino acids in the polypeptide chain of the invention, the most appropriate methods of production are the synthetic methods for building up the chains described above.

The polypeptides of the present invention have a particular application in vaccinating patients against diseases caused by enteroviruses, in particular polioviruses. Vaccination is achieved by administering to a patient an effective amount of a synthetic polypeptide of the invention, either as such or linked to a carrier. Typically, from 100 µg to 1 mg of the polypeptide is administered to a human.

When used for this purpose, the material must be such, particularly of such a size, that it will produce an immune reaction. The polypeptide will usually therefore be coupled to an immunogenically active carrier such as the proteins mentioned hereinbefore or be in the form of a longer polypeptide including the polypeptide sequence, which may be achieved by linking the polypeptide to a synthetic polypeptide such as poly-lys. Although it has been indicated that the polypeptides of the present invention, when in immunogenic form, can act to protect a patient by inducing the production of the appropriate antibodies, it is possible that, in addition, the polypeptide may have a chemotherapeutic effect. Thus it is believed that the same polypeptide sequence which can evoke the appropriate antibodies to be formed may be the sequence in the viral capsid protein which enables the virus to attach itself to a cell within a patient and thereby cause the infection. Thus the polypeptide of the present invention may have a competitive effect and, by occupying the appropriate cell receptor sites, prevent the virus itself from infecting the patient. Generally, the immunogens including the polypeptides of the present invention will be administered by injection which will usually be intramuscular but can be by other routes, such as intraperitoneally or subcutaneously.

The polypeptides of the present invention can also be used to prime the immune system of a patient to exhibit an enhanced response to vaccination against diseases caused by enteroviruses. An effective amount, typically 100 µg to 1 mg, of a polypeptide of the invention can be administered to a patient and, after a suitable amount of time has elapsed, the patient can be vaccinated against a disease caused by a corresponding enterovirus in the conventional manner. Less material, both of the polypeptide of the invention and of that required for the conventional vaccination, may be needed and fewer challenges may be required to achieve effective vaccination.

The present invention also provides a pharmaceutical composition which includes a synthetic polypeptide of the present invention as active ingredient, together with a pharmaceutically acceptable carrier or diluent. The actual form of the peptide in this composition, i.e. whether it is linked to another compound or not, will depend upon the use to which the composition is to be put.

An alternative use for the polypeptides of the present invention is in the diagnosis of infection by enteroviruses. This diagnosis will be carried out by the detection of presence or absence of antibody to the appropriate virus in the patient. For this purpose, the peptides will usually be bonded to inert carriers as mentioned hereinbefore and, in such form, they can also be used as an affinity chromatography medium in the isolation of antibodies to the virus. The synthetic polypeptide of the invention may therefore form a component of a test kit, suitable for use in determining antibody against an enterovirus, which kit also includes means for determining antibody bound to the polypeptide. Any suitable immunoassay system, for example radioimmunoassay system, may be used to determine the antibody.

Thus, in a further aspect, the present invention provides the polypeptide of the invention for use in a method of treatment or diagnosis of humans or animals. The method of treatment will generally involve vaccination to induce an antibody response thereby preventing the patient from becoming infected subsequently by the virus, while the diagnosis method will involve the detection of antibody to the virus caused as a result of infection. In view of the possible chemotherapeutic function of the polypeptide, the method of treatment may also involve administration of material including the polypeptide to a patient already exposed to the virus and possibly even also after the onset of symptoms.

The vaccines administered to patients will preferably include not just one polypeptide in accordance with the present invention, but at least two and preferably more. By including several different polypeptides, for example one for each of the three different types of poliovirus, this could enable the patient to be vaccinated against all three types of poliovirus and the vaccine can also take account of variations in the polypeptide between different viruses of the same type. It is also preferred to formulate compositions as physical mixtures which include other antigens particularly those commonly used in infant vaccines, such as tetanus, diphtheria and whooping cough. However, as indicated before, such antigens may, if desired, be linked chemically to the polypeptide of the invention in order to render it immunogenic.

BRIEF DESCRIPTION OF DRAWING

The Figure of the accompanying drawing shows the RNA sequence for the VP1 capsid protein in the poliovirus type 3 Sabin strain (Leon) as determined by the present inventors. Within this sequence, the oligonucleotide of codons 93 to 100 is marked by underlining.

MODES, INCLUDING THE BEST MODE, FOR CARRYING OUT THE INVENTION

Examples 1 and 2 below show how the eight amino acid region coded for by codons 93 to 100, including the region coded for by codons 93 to 98, in the RNA sequence coding for the VP1 capsid protein of poliovirus type 3 Sabin strain (Leon) was identified by the present inventors as a major antigenic site involved in enterovirus neutralisation.

Examples 3 to 6 illustrate modes, including the best mode, for carrying out the invention.

EXAMPLE 1

Monoclonal antibodies specific for type 3 poliovirus (P3-Leon-USA-1937) were produced. Mutants of the single parental poliovirus type 3 strain were selected in the presence of several individual virus neutralising monoclonal antibodies. Sixteen mutant groups were identified by their distinct patterns of resistance against the monoclonal antibodies. Their reaction patterns are presented in Table 2. This Table also identifies the monoclonal antibodies used to select the various groups of mutant viruses, as evidenced by the fact that such mutants would not be neutralised at all by the selecting monoclonal antibody and several others. The fact that these mutants had lost their ability to be neutralised by at least one of the collection of monoclonal antibodies is evidence to support the fact that at least one base change has probably occurred in the antigenic site. These findings were interpreted as showing that the neutralisation of poliovirus by antibody involves a single antigenic site. The RNA of representative strains from each mutant group was sequenced to define more precisely the positions of amino acid substitutions in VP1 which conferred resistance. This was done by the dideoxy sequencing method using a primer restriction-fragment prepared from cloned poliovirus cDNA.

The RNA of representative strains of each mutant group was sequenced in the region of 393 to about 240 bases downstream from the 5' end of the VP1 coding region of the genome. The dideoxy sequencing method was used, using a restriction fragment primer prepared from cloned poliovirus cDNA. The primer was prepared by digesting plasmid DNA with Ecor RI and Sphl and labelled by incubation with 1 unit of Klenow fragment from DNA polymerase 1 and 100 $\mu$Ci of ($\alpha^{32}$P) dATP (3000 Ci/mmol; Amersham International). The products were denatured and loaded onto a preparative slab poly-acrylamide gel. After electrophoresis the 47 base restriction fragment was detected by autoradiography, excised and eluted from the gel. The primer was purified by exclusion chromatography and then annealed onto the virion RNA and incubated with dideoxyribonucleotides and deoxyribonucleotides in appropriate proportions together with 5 units of Avian Myeloblast Reverse Transcriptase (Life Sciences Inc). Following incubation at 37° C. for 25 minutes the reaction products were denatured and loaded onto sequencing gels. After electrophoresis the gels were fixed in 10% acetic acid, washed and dried and subjected to autoradiography.

The sequences of all the mutants were the same except for the single point mutations shown in Table 3. Where mutations were detected there was only one per mutant and all would result in amino acid substitutions.

Base changes were detected in viruses of fifteen of the sixteen mutant groups and were concentrated into a region of only eight codons, positions 4 to 11 in Table 3 which correspond to codons 93 to 100 of the parental poliovirus type 3 Sabin strain. It was thus concluded that the amino acid sequence coded for by codons 93 to 100 represents the antigenic site.

The complete sequence of the VP1 genome is given in attached Figure of the accompanying drawings.

Table 3 also shows the amino acid sequence and codon sequence for the antigenic site for poliovirus type 1 (Mahoney strain). The relevant positions are positions 4 to 11. These correspond to codons 95 to 102.

EXAMPLE 2

Identification of the amino acids required for the neutralization of poliovirus by the specific monoclonal antibodies employed in Example 1

The mutants of Example 1 were classified according to whether they were neutralized, or not, by antibody 25-1-14. The results are shown in Table 4. It can be seen that all substitutions at positions 4, 7 and 9 (corresponding to codons 93, 96 and 98) produced viruses which this antibody did not neutralize. Conversely substitutions at position 10 (codon 99) had no effect on neutralization. In addition, substitutions in position 8 (codon 97), by amino acids lacking hydroxyl groups, were associated with lack of neutralization. The effect of substitutions at position (codon 100) 11 was ambiguous. It was therefore concluded that antibody 25-1-14 required glutamic acid at position 4, threonine at position 7, threonine or serine at position 8 and arginine at position 9 for its neutralizing activity.

The results of a similar analysis of all eleven monoclonal antibodies used for the analysis of the mutants are summarized in Table 5. It can be seen that the amino acids at positions 4 and 9 in particular effected neutralization of the mutant viruses. In addition, six antibodies neutralized mutants having a serine in place of the threonine at position 8 while not neutralizing viruses with other substitutions at this position. A seventh antibody (208) did not neutralize viruses with any substitution at this position. This is consistent with the view that hydroxy amino acids are important in binding of neutralizing antibody to the virus. The majority of the required amino acids were polar in nature as expected for the residues participating in the reaction of antibody with antigen. This supports the view that the eight amino acid sequence on VP1 represents the site on the virus to which neutralizing antibodies bind.

EXAMPLE 3

The following polypeptides S1, S2, S5 and S6 according to the present invention were synthesized by the standard method employing a Merrifield resin:

S1:

H-Ala-Ile-Ile-Glu-Val-Asp-Asn-Glu-Gln-Pro-Thr-Thr-Arg-Ala-Gln-Lys-Leu-Phe-OH;

S2:

H-Glu-Gln-Pro-Thr-Thr-Arg-Ala-Gln-Lys-OH;

S5:

H-Asn-Glu-Gln-Pro-Thr-Thr-Arg-Ala-Gln-Lys-Leu-Phe-Ala-Met-Trp-Ile-Cys-OH; and

S6:

H-Asn-Glu-Gln-Pro-Thr-Thr-Arg-Ala-Gln-Lys-OH.

300 μ moles of the resin yielded 180 mg of S1, 250 mg of S2, 190 mg of S5 and 240 mg of S6. The polypeptides were purified by washing through a Sephadex column using 50% (v/v) acetic acid.

EXAMPLE 4

Preparation of oligopeptides S10 and S10a

S10:

H-Glu-Val-Asp-Asn-Glu-Gln-Pro-Thr-Thr-Arg-Ala-Gln-Lys-Leu-Phe-Ala-Cys-OH (III)

S10a:

H-Cys-Glu-Val-Asp-Asn-Glu-Gln-Pro-Thr-Thr-Arg-Ala-Gln-Lys-Leu-Phe-Ala-Cys-OH (a) Preparation of solid phase support Polydimethylacrylamide gel resin (a copolymer of dimethylacrylamide-ethylenebisacrylamide-acryloylsarcosine methyl ester; containing 0.3 milliequivalents of sarcosine per gram resin) was treated with ethylenediamine overnight. After thorough washing, 9-fluorenylmethyloxycarbonyl (Fmoc)-valine was added as an internal standard. After cleavage of the Fmoc group the acid labile linkage agent, 4-hydroxymethylphenoxyacetic acid, was added as its symmetrical anhydride. After thorough washing this afforded a low-loading acid labile resin (Cambridge Research Biochemicals Ltd, Button End Industrial Estate, Harston, Cambridgeshire, UK).

(b) Preparation of protected oligopeptides of formula (III) and (IV)

(III):

H-Glu-Val-Asp-Asn-Glu-Gln-Pro-Thr-Thr-Arg($NO_2$)-Ala-Gln-Lys-Leu-Phe-Ala-Cys($Bu^t$)-OH (IV):

H-Cys($Bu^t$)-Glu-Val-Asp-Asn-Glu-Gln-Pro-Thr-Thr-Arg($NO_2$)-Ala-Gln-Lys-Leu-Phe-Ala-Cys($Bu^t$)-OH

The partially protected peptides (III) and (IV) were synthesised by the Fmoc-polyamide method of solid phase peptide synthesis (Arshady et al, J.C.S. Perkin I, 529 (1981); Atherton et al, J.C.S. Perkin I, 538 (1981); Atherton et al, J.C.S. Perkin I 65 (1983); Brown et al, J.C.S. Perkin I, 75 (1983); Brown et al, J.C.S. Perkin I, 1161 (1983)) using the polyamide gel resin prepared above.

Fmoc-amino acids were coupled (in a twelve fold excess) as their preformed symmetrical anhydrides: the Fmoc-amino acid (2 equiv) was dissolved in dichloromethane with a few drops of N,N-dimethylformamide (DMF) if required to aid dissolution. N,N-Dicyclohexylcarbodiimide (DCC) (1 equiv) was added and the mixture stirred at room temperature for 10 minutes. The precipitated N,N-dicyclohexylurea (DCU) was filtered off, the filtrate evaporated to dryness and the residue dissolved in DMF. The solution was added to the deprotected and washed resin and the coupling reaction allowed to proceed. The coupling of the first residue to the derivatised resin was carried out in the presence of N,N-dimethylaminopyridine (DMAP) (1 equiv) which acted as a catalyst.

Asparagine and glutamine residues were added as follows: 1-hydroxybenzotriazole (HOBT) (1 equiv) and DCC (1 equiv) were dissolved in DMF at 0° C. After stirring for ten minutes at 0° C. a solution of Fmoc-asparagin (or glutamine) (1 equiv) in DMF was added. This mixture was stirred for a further 10 minutes at 0° C. and then the entire mixture added to the resin and coupling allowed to proceed. A typical synthetic cycle was as follows:

| Reagent | Duration | Operation |
|---|---|---|
| DMF | 5 × 1 min | Wash |
| 10% Piperidine/DMF | 1 × 3 min + 1 × 7 min | Deprotection |
| DMF | 10 × 1 min | Wash |
| Preformed symmetrical anhydride or active ester | 60–120 min | Coupling |
| DMF | 5 × 1 min | Wash |

The completeness of coupling at each stage was monitored by the Kaiser test.

The quantites used were as follows: Acid labile resin (1.0 g; 0.3 mmol) and Fmoc-amino acid (3.6 mmol). Each cycle was carried out on the following basis:

| Fmoc—amino acid—OH | Quantities | Coupling Time |
|---|---|---|
| 1. Fmoc—Cys($Bu^t$)—OH | 1.44 g; 3.6 mmol | 1 hours |
| 2. Fmoc—Ala—OH | 1.12 g; 3.6 mmol | 1 hour |
| 3. Fmoc—Phe—OH | 1.40 g; 3.6 mmol | 1 hour |
| 4. Fmoc—Leu—OH | 1.27 g; 3.6 mmol | 1.5 hours |
| 5. Fmoc—Lys(Boc)—OH | 1.69 g; 3.6 mmol | 1.5 hours |
| 6. Fmoc—Gln—OH | 0.66 g; 1.8 mmol | 1 hour |
| 7. Fmoc—Ala—OH | 1.12 g; 3.6 mmol | 1.5 hours |
| 8. Fmoc—Arg(NO2)—OH | 1.59 g; 3.6 mmol | 1.5 hours |
| 9. Fmoc—Thr($Bu^t$)—OH | 1.43 g; 3.6 mmol | 1.5 hours |
| 10. Fmoc—Thr($Bu^t$)—OH | 1.43 g; 3.6 mmol | 1 hour |
| 11. Fmoc—Pro—OH | 1.22 g; 3.6 mmol | 1 hour |
| 12. Fmoc—Gln—OH | 0.66 g; 1.8 mmol | 1 hour |

-continued

| Fmoc—amino acid—OH | Quantities | Coupling Time |
| --- | --- | --- |
| 13. Fmoc—Glu(OBu$^t$)—OH | 1.53 g; 3.6 mmol | 1 hour |
| 14. Fmoc—Asn—OH | 0.64 g; 1.8 mmol | 1 hour |
| 15. Fmoc—Asp(OBu$^t$)—OH | 1.48 g; 3.6 mmol | 1 hour |
| 16. Fmoc—Val—OH | 1.22 g; 3.6 mmol | 1 hour |
| 17. Fmoc—Glu(OBu$^t$)—OH | 1.53 g; 3.6 mmol | 1 hour |

As the C-terminal heptadecapeptide sequence is common to both oligopeptides (II) and (IV), the resin was split in half after deprotection, at the end of cycle 17 and to half is added:

| Fmoc—amino acid—OH | Quantities | Coupling Time |
| --- | --- | --- |
| 18. Fmoc—Cys(Bu$^t$)—OH | 0.72 g; 1.8 mmol | 1 hour |

After deprotection and washing both peptide resins were shrunk by washing with dichloromethane and diethylether. Treatment with 90% aqueous trifluoroacetic acid (TFA) at room temperature for 1 hour afforded after work up the peptides (III) and (IV) (138 and 159 mg respectively).

Both peptides (III) and (IV) were checked by high performance liquid chromatography (hplc) and fast atom bombardment mass spectrometry (FAB-MS). Hplc ($\mu$ Bondapak $C_{18}$; 25% $CH_3CN$ 75% 0.01 M $NH_4OAc$, pH4.5; isocratic) indicated that the purity of the peptides was greater than 90%. Molecular ions in the FAB-MS for peptide (III) at 2050 and for peptide (IV) at 2209 indicated both peptides had the correct molecular weights, i.e. 2049 and 2208 respectively. Both spectra also showed signals 45 mass units lower due to the loss of a nitro group from the arginine residue with subsequent reprotonation.

(c) Preparation of Peptides S10 and S10a

Peptides (III) and (IV) were cleaved from the polyamide gel resin and fully deprotected using liquid hydrogen fluoride in the presence of anisole as a scavenger. This afforded on work up, peptides S10(78 mg) and S10a(85 mg) respectively. No further purification was effected. On hplc ($\mu$ Bondapak $C_{18}$; 20% $CH_3CN$, 80% 0.01 M $NH_4OAc$, pH4.5, isocratic) a single major component was indicated for both compounds with an estimated purity of greater than 80%. Thin layer chromatography in various systems showed the products to be essentially homogeneous. Molecular ions were observed using FAB-MS at 1949 for peptide S10 and at 2052 for peptide S10a. This was consistent with the peptides having molecular weights of 1948 and 2051 respectively. Signals of approximately equal intensity were observed at 18 mass units lower than the molecular ions for both peptides. This phenomenon was unexplained although almost certainly represents a fragmentation signal rather than indicating any impurity due to its being common to both peptides. As both peptides contained cysteine moieties, which seldom exist solely in their reduced state the FAB-Ms was run at high field in order that any dimer present might be observed-this was not the case for either peptide.

EXAMPLE 5

Preparation of oligopeptides S11 and S12

S11:
H-Ala-Ile-Glu-Val-Asp-Asn-Glu-Gln-Pro-Thr-Thr-Arg-Ala-Gln-Lys-OH
S12:
H-Glu-Gln-Pro-Thr-Thr-Arg-Ala-Gln-Lys-Leu-Phe-Ala-Met-Trp-Arg-Ile-OH

These above peptides were synthesised in the same manner as described in Example 4.

(a) Preparation of S11

The quantities used were as follows: acid labile resin (0.5 g; 0.15 mmol), Fmoc-amino acid (1.8 mmol), DCC (0.19 g; 0.9 mmol), DMAP (0.11 g, 0.9 mmol), and HOBT (0.12 g, 0.9

| Fmoc—amino acid—OH | Quantities | Coupling Time |
| --- | --- | --- |
| Fmoc—Lys(Boc)—OH | 0.84 g; 1.8 mmol | 1 hour |
| Fmoc—Gln—OH | 0.33 g, 0.9 mmol | 1 hour |
| Fmoc—Ala—OH | 0.56 g, 1.8 mmol | 1 hour |
| Fmoc—Arg($NO_2$)—OH | 0.79 g, 1.8 mmol | 1 hour |
| Fmoc—Tyr(Bu$^t$)—OH | 0.72 g, 1.8 mmol | 1 hour |
| Fmoc—Tyr(Bu$^t$)—OH | 0.72 g, 1.8 mmol | 1 hour |
| Fmoc—Pro—OH | 0.33 g, 0.9 mmol | 1 hour |
| Fmoc—Gln—OH | 0.33 g, 0.9 mmol | 1 hour |
| Fmoc—Glu(OBu$^t$)—OH | 0.77 g, 0.9 mmol | 1 hour |
| Fmoc—Asn—OH | 0.32 g, 1.8 mmol | 1 hour |
| Fmoc—Asp(OBu$^t$)—OH | 0.74 g, 1.8 mmol | 1 hour |
| Fmoc—Val—OH | 0.61 g, 1.8 mmol | 1 hour |
| Fmoc—Glu(OBu$^t$)—OH | 0.77 g, 1.8 mmol | 1 hour |
| Fmoc—Ile—OH | 0.64 g, 1.8 mmol | 1 hour |
| Fmoc—Ala—OH | 0.56 g, 1.8 mmol | 1 hour |

After completion of the synthesis the peptide resin was shrunk by washing with dichloromethane and diethyl ether.

The peptide was cleaved from the resin and the acid labile side chain protecting groups were removed by treating the peptide resin with 90% aqueous trifluoroacetic acid for 1 hour at room temperature. After filtration, evaporation of the solvent afforded a residue which on trituration with diethyl ether afforded oligopeptide (V) as a white solid (152 mg). Hplc ($\mu$ Bondapak $C_{18}$, linear gradient 5–95% $CH_3CN$-0.01 M $NH_4OAc$, pH 4.5 over 15 minutes) showed the product to be essentially homogeneous.

This material was dissolved in 80% acetic acid (15 $cm^3$), 10% Pd/C (150 mg) added and hydrogen bubbled through the stirred suspension for 15 hours. Catalyst filtered off, filtrate evaporated and residue triturated with diethyl ether affording SII as an off-white solid (102 mg). Hplc of this material under the same conditions as above showed an essentially homogeneous compound. FAB-mass spectrometry gave a sharp molecular ion at m/e 1812 which is consistent with a molecular weight of 1811.
H-Ala-Ile-Ile-Glu-Val-Asp-Asn-Glu-Gln-Pro-Thr-Thr-Arg($NO_2$)-Ala-Gln-Lys-OH(V)

(b) Preparation of S12

The quantities used were as follows: acid labile rsin (0.5 g; 0.25 mmol) Fmoc-amino acid (1.8 mmol) DCC (0.19 g; 0.9 mmol); DMAP (0.11 g; 0.9 mmol) and HOBT (0.12 g; 0.9 mmol)

| Fmoc—amino acid—OH | Quantities | Coupling Time |
| --- | --- | --- |
| Fmoc—Ile—OH | 0.61 g; 1.8 mmol | 1 hour |
| Fmoc—Arg($NO_2$)—OH | 0.79 g; 1.8 mmol | 1 hour |
| Fmoc—Trp—OH | 0.77 g; 1.8 mmol | 2 hours |
| Fmoc—Met—OH | 0.67 g; 1.8 mmol | 1 hour |
| Fmoc—Ala—OH | 0.56 g; 1.8 mmol | 1 hour |
| Fmoc—Phe—OH | 0.71 g; 1.8 mmol | 1 hour |
| Fmoc—Leu—OH | 0.64 g; 1.8 mmol | 1.5 hours |
| Fmoc—Lys(Boc)—OH | 0.84 g; 1.8 mmol | 1 hour |
| Fmoc—Gln—OH | 0.33 g; 0.9 mmol | 1 hour |

-continued

| Fmoc—amino acid—OH | Quantities | Coupling Time |
|---|---|---|
| Fmoc—Ala—OH | 0.56 g; 1.8 mmol | 1 hour |
| Fmoc—Arg—OH | 0.79 g; 1.8 mmol | 1 hour |
| Fmoc—Thr(Bu$^t$)—OH | 0.72 g; 1.8 mmol | 1.5 hours |
| Fmoc—Thr(Bu$^t$)—OH | 0.72 g; 1.8 mmol | 1 hour |
| Fmoc—Pro—OH | 0.61 g; 1.8 mmol | 1 hour |
| Fmoc—Gln—OH | 0.33 g; 0.9 mmol | 2 hours |
| Fmoc—Glu(OBu$^t$)—OH | 0.77 g; 1.8 mmol | 1 hour |

After final deprotection, resin washed and shrunk as before.

Cleavage of peptide from resin carried out using 90% aqueous trifluoroacetic acid containing few drops of anisole. This afford oligopeptide (VI) as an off white solid (117 mg). Hplc ($\mu$ Bondapak $C_{18}$, 35% $CH_3CN$ 65% 0.01 M $NH_4OAc$, pH 4.5) showed a single peak. Product was also homogeneous on tlc.

Hydrogenation carried out as before affording, after work up, the peptide S12 product IV as a pale fawn solid (93 mg). Hplc ($\mu$ Bondapak $C_{18}$, linear gradient 5–95% $CH_3CH$ 0.01 M $NH_4$ OAc, pH 4.5 over 15 minutes) showed the product to be essentially homogeneous. FAB-mass spectrometry gave a signal at m/e 1975 consistent with a molecular weight of 1974.

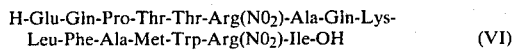

H-Glu-Gln-Pro-Thr-Thr-Arg(NO$_2$)-Ala-Gln-Lys-Leu-Phe-Ala-Met-Trp-Arg(NO$_2$)-Ile-OH    (VI)

EXAMPLE 6

Measurement of Specific Antibody Responses

The specific antibody responses of laboratory rabbits to peptides S10 and S10a were measured in respect to:
1. Antibody to uncoupled peptide (S10 or S10a) detected by enzyme-linked immunoabsorbent assay (ELISA) tests.
2. Antibody to polioviruses of types 1, 2 and 3 as detected by:
   (a) antigen blocking assays against poliovirus D and C antigen measured in single-radial-diffusion (SRD) tests in gels;
   (b) immuno-double-diffusion tests in gels;
   (c) immune-electron microscopy;
   (d) virus neutralization tests in tissue cultures.

Coupling of peptide of bovine thyroglobulin 1 ml of 0.1 M sodium phosphate buffer pH 7.5 was added to a glass vial containing 30 mg of bovine thyroglobulin (BTG, Sigma). The dissolved material was transferred with 1 ml sodium phosphate buffer washing to a second vial containing 10 mg of peptide (S10, S10a) to give a final volume of 2 ml peptide-BTG solution. The vial was wrapped in aluminium foil to exclude light. A solution of 2% glutaraldehyde was made in 0.1 M sodium phosphate buffer pH 7.5 and 200 $\mu$ added to the peptide-BTG solution in four lots of 50 $\mu$l, shaking between additions, and then left for 1 hour at room temperature with intermittent shaking. The solution was then dialysed against one litre of phosphate buffered saline (PBS) at 40 overnight, and then against 1 litre of fresh PBS for a further eight hours. Coupled peptide was stored at −70° C. until required.

Coupled oligopeptides used for immunization of experimental animals

Synthetic oligopeptides S10 and S10a were conjugated separately to bovine thyrogobulin (BTG) as described above. The preparations used for immunization contained 500 $\mu$g/ml of peptide S10 or S10a and 1500 $\mu$g/ml of BTG suspended in phosphate buffered saline (pH 7.2).

Immunization schedule for experimental animals

Young (5–6 months of age) healthy rabbits were injected intramuscularly with an initial dose of 0.5 ml coupled peptide mixed with an equal volume of Freunds complete adjuvant (FCA, Bacto) and subsequently injected with booster doses (0.5 ml) coupled peptide or uncoupled peptide adsorbed to Al(OH)$_3$ (0.5 ml) according to the following schedule. Serum samples for analysis were collected at intervals up to 62 days after the first injection.

| Day 0 | 0.5 ml coupled peptide + FCA | serum sample |
|---|---|---|
| Day 14 | — | serum sample |
| Day 17 | 0.5 ml coupled peptide | — |
| Day 27 | — | serum sample |
| Day 30 | 0.5 ml coupled peptide | — |
| Day 41 | — | serum sample |
| Day 48 | uncoupled peptide + Al(OH)$_3$ | —Day 55 |
| — | serum sample | |
| Day 62 | — | serum sample |

Enzyme immunoassays (ELISA) for antibody to oligopeptide

Enzyme immunoassays were carried out to investigate the immune response of the rabbit to the peptide. Rabbit sera were examined for antibody which bound to oligopeptide linked to polyvinyl plates by glutaraldehyde. The bound antibody was detected by the addition of anti rabbit antibodies which were coupled to an enzyme, $\beta$-galactosidase. On addition of substrate for the $\beta$-galactosidase (ortho-nitrophenyl-$\beta$-D-galactoside) a colorimetric change takes place, the intensity of which is proportional to the amount of antibody bound to peptide.

Ninety-six well Microelisa plates (Dynatech) were treated with 0.2% glutaraldehyde in PBS for 33 hours. Plates were washed ×2 in PBS and oligopeptide added (10 ug/ml). After incubation overnight at room temperature plates were washed ×5 with PBS containing 0.5% Tween 20 (Koch-Light Laboratories, Colnbrook, Berks). Dilutions of rabbit sera in PBS containing 0.01% sodium azide were added to wells and incubated overnight at room temperature. Plates were washed ×5 with phosphate buffered saline containing 0.5% Tween 20 and donkey anti rabbit Ig linked to $\beta$-galactosidase (Amersham International) diluted in PBS pH 7.5 containing 0.1% Tween 20 10 mM MgCl$_2$ and 1 mM 2-mercaptoethanol added. After 3 hrs at 37 degrees centigrade the conjugated antibody was removed, the plates washed ×5 with phosphate buffered saline containing Tween 20. The substrate, ortho-nitrophenyl-$\beta$-D- galactoside (3 mM in phosphate buffered saline pH 7.5 containing 10 mM MgCl$_2$ and 0.1 M 2 mercaptoethanol) was added to each well and plates incubated at 37 degrees centigrade until colour devloped. Optical density was read on a Titertek multiscan set at 410 nm. The machine was 'blanked' using substrate and serum dilutions considered positive if the optical density was greater than that of a 1:100 dilution of normal rabbit serum collected from the animal prior to immunization of the peptide.

Antigen blocking assays for antibody to poliovirus D and C antigen employing single radial diffusion (SRD) in gel The rabbit sera were tested in SRD antigen-blocking tests to determine their reactivities with 'D' and 'C' antigens of poliovirus 3. The method used was a modification of the autoradiographic SRD method of Schild et al (1980) as described elsewhere (Ferguson et al 1982). Briefly, [$^{35}$S]-methionine labelled 155S 'D' or 80S 'C' peaks of poliovirus antigen from sucrose gradients were mixed with the test monoclonal antibody before adding to wells in agarose gels containing low concentrations of hyperimmune anti-poliovirus type 3 serum. Diffusion of radiolabelled antigen in the gel after 24–48h was detected by autoradiography. Test antibody which reacts with 'D' and/or 'C' antigen inhibits its diffusion into the gel compared with control antigen treated with phosphate buffered saline alone. The antigen blocking titre are assessed as the dilution of serum which significantly reduces the zone size in comparison with zones produced with control antigen mixed with phosphate buffered saline.

Immuno-double-diffusion assays

These were performed in agarose gels using the methods described by Schild et al (1971) and Schild (1972). The antigens used were concentrates of poliovirus types 1, 2 and 3 prepared as described by Schild et al (1980).

Virus neutralization tests

These were performed by standard methods Domok and Magrath (1979) in Hep2c cell monolayers in the wells of 96 well microtitre plates. The challenge dose of virus was 100 tissue culture infectious doses 50% per well.

Immune electron microscopy

Concentrated and purified D antigen of poliovirus type 3 (P3/Leon/USA/37) prepared as described by Minor et al (1980) were mixed with equal volumes of rabbit sera undiluted or diluted 1:10 and held at 37 degrees centigrade for 45 minutes. 10 μof mixture was placed on carbon film-coated electron microscope grids and allowed to attach for 2 minutes. Excess mixture was removed by blotting by filter paper and the specimen negatively stained for 15 secs with 4% aqueous sodium silico tungstate (pH 7.4). The grids were allowed to dry and were examined under a Philips Model 201 electron microscope. The presence of virus aggregates was recorded.

RESULTS

Induction of antibody to homologous peptide

The titres of antibody to oligopeptide S10 determined by ELISA assay are shown in Table 6 for representative animals. Fourteen days following the initial immunization with S10 or S10a all animals had readily demonstrable antibody to peptide S10. The titres had increased by day 27 and in later serum samples following booster doses of the oligopeptides. In ELISA tests using peptide S10a the antibody titres were closely similar to those obtained with S10. No anti-peptide antibody was detected in control animals immunized with BTG alone (i.e. without coupled oligopeptides).

Induction of antibody to poliovirus (a) Antigen blocking antibody

Antibody specific for infectious poliovirus particles (D antigen) or empty virions (C antigen) may be detected by antigen blocking assays employing the single radial diffusion test (Schild et al 1980, Ferguson et al 1982). This method was applied to sera obtained from animals immunized with oligopeptides S10 and S10a coupled to BTG.

Table 7 shows the induction of blocking antibody to poliovirus type 3 D and C antigens in rabbits injected with oligopeptides S10 and S10a in the immunization schedule described above. Antibody reacting with and blocking diffusion of poliovirus type 3 D antigen first appeared between the 14th and 27th day after commencement immunization (i.e. following two doses of antigen). One animal (rabbit No. 52) produced antibody to C antigen only and four animals shown in the table producd antibody to both D and C antigen to similar titres. The antibody was type specific for poliovirus type 3, none of the animals developed blocking activity against the D or C antigens of polioviruses of types 1 or 2.

(b) Immuno-double-diffusion tests

Immuno double diffusion tests are widely used in virology to detect specific reactions of viral antigens and antibodies (Schild and Dowdle 1975). These tests have been applied to poliovirus D antigens and specific antisera (Beale and Mason 1962). The sera from rabbits immunized with oligopeptides S10 and S10a were tested against viral antigens. The observed precipitin reactions are recorded in Table 8.

Sera collected from rabbits on day 41, 55 and 62 after commencement of immunization gave clear precipitin reactions (Table 8) when tested with concentrates of poliovirus type 3(P3/Saukett/USA/50) which contained essentially D antigen particles (Minor et al 1980, Schild et al 1980). They failed to react with concentrates of poliovirus type 1 or type 2.

Sera collected prior to commencement of immunization or 14 days later failed to give such reactions whilst a proportion of sera collected at 27 days gave reactions. To test the specificity of the reactions the sera collected on day 55 from rabbits 53, 55 and 57 were tested against a wider range of poliovirus 3 strains. The results are shown in Table 9. The sera reacted with all poliovirus type 3 strains tested but did not react with poliovirus type 1 or 2. The antibodies were thus poliovirus type 3 specific, but were broadly reactive for different strains of type 3 virus.

To further test the identity of the precipitin line antisera from rabbits 55 and 57 collected on day 55 and 62 after commencement of immunization were tested in wells adjacent to wells in which polyclonal goat antiserum to purified poliovirus 3 virus (Sabin vaccine strain) had been added. The lines given by the rabbit sera showed continuity with those given by the polyclonal goat serum. Since the antigen preparation used (A/Saukett/USA/50 virus) contained essentially D antigen particles it was concluded that the rabbit reacted with D antigen. This conclusion was confirmed by using as antigens in the precipitin tests purified D and C antigens labelled with $^{35}$S methionine (Minor et al 1980). The purified D antigen gave precipitin lines which were clearly demonstrated by auto-radiography.

Heating poliovirus D antigen particles at 56 degrees centigrade for 5 min is known to quantitatively convert its antigenic characteristics to that of C antigen (Le Bouvier 1955). Immuno double diffusion reactions were performed using appropriately heated concentrates of P3/Saukett/USA/50 and P3/Leon/USA/37. Sera which gave immunoprecipitin lines corresponding to poliovirus 3 D antigen also gave lines corresponding to C antigen when tested against heated virus. These findings are consistent with the results of the SRD antigen blocking tests in which specific anitbody to both D and C antigen were detected in the rabbit sera.

(c) Immune electron microscopy

Sera from rabbits 55 and 57 collected 5 days after commencement of immunization with oligopeptide produced clear aggregates of virus P3/Leon/USA/37 virus particles. No such aggregates were seen in control preparation of virus treated with phosphate buffered saline only or treated with serum collected at day 0 from the same animals (Nos. 55 and 57) when the virus particles were seen to be widely dispersed. The findings were interpreted as indicating that the rabbit sera contained antibodies to poliovirus type 3 capable of cross-linking and aggregating virus particles. The distance between individual particles in aggregates (10–15 nm) were consistent with dimensions of immunoglobulin molecules. Many particles were seen to be surrounded by a 'halo' of material which was interpreted as attached antibody. An identical appearance was seen when know specific antibodies, e.g. monoclonal antibodies to poliovirus 3 were added to the virus.

(d) Virus neutralization tests

Table 10 shows the neutralization titres detected in microtitre assays against poliovirus 3 strains in four rabbits immunized with oligopeptides S10 and S10a. Neutralizing activity was detected in a proportion of animals at day 41 post immunization and was present in all sera collected from 55 days onwards. The titres against the two poliovirus type 3 strains were similar although they are known (Minor et al 1982) to differ antigenically as indicated by their reactions with monoclonal antibodies. The findings are thus consistent with the results of immuno-double-diffusion tests which indicated that the antibody to poliovirus 3 induced by the oligopeptides reacts broadly within the type. The neturalizing activity was type specific; no neutralization of poliovirus type 1 and 2 strains was detected with any serum.

In conclusion, rabbits injected with oligopeptides S10 and S10a developed specific anti-peptide antibodies. In addition they developed antibodies which reacted with poliovirus type 3 D and C antigens as indicated by (a) antigenic blocking assays, (b) immuno precipitin tests, (c) immune electron microscopy. The antibodies were type specific for poliovirus type 3 but failed to react with polioviruses of types 1 or 2. Wherever tested (e.g. in immuno double diffusion tests and neutralization tests) the antibodies reacted broadly with all type 3 poliovirus strains examined. The sera neutralized infectivity of poliovirus type 3. Neutralization was specific for poliovirus type 3 but was detected with all type 3 polioviruses tested.

EXAMPLE 7

Evidence that an oligopeptide S1 primes guinea pigs for production of a neutralizing antibody response to small doses of poliovirus 3 D antigen Oligopeptide S1 was coupled to bovine thyroglobulin by the method described in Example 6. Guinea pigs were immunized intraperitoneally with 250 $\mu$g of oligopeptide coupled to 500 $\mu$g bovine thyroglobulin. Immunization was given on day 0, day 14, day 28 and day 42. For the first two immunizations the coupled peptide was administered with FCA (Bacto) and for the later two immunizations no adjuvant was used. Sixty days after the last dose of oligopeptide the animals were injected with a small dose of inactivated poliovirus type 3 Leon/USA/37 prepared as purified D antigen (Minor et al 1980). The quantity of antigen injected was 1 D antigen unit assayed as described by a single-radial-diffusion test (Schild et al 1981).

Control animals were prepared by immunization in a similar way but with 500 $\mu$g doses of BTG without oligopeptide. Immediately before and one week after injection of poliovirus 3 the animals were bled and the sera tested for neutralizing antibody to the P3/Leon/USA/37.

No animals possessed neutralizing antibody at a titre 1:20 at the time of injection of virus. One week after injection of virus animals prepared with oligopeptide had titres varying from 200 to 24,000. Corresponding titres in the control animals ranged from 3–200.

The results are shown in Table 11. It was concluded that animals prepared by prior injection of BTG-coupled oligopeptide S1 developed higher antibody titres than the control animals prepared by injection of BTG alone and that this was due to the priming effect of previous injection of synthetic oligopeptide S1.

REFERENCES

Beale, A. J. and Mason, P. J. (1962) Journal of Hygiene 60 113–120

Le Bouvier G. (1955) Lancet 2 1013–1016

Domok, I. and Magrath, D. I. (1979) WHO offset publication No. 46.

Ferguson, M., Qui Yi Hua, Minor, P. D., Magrath, D. I., Spitz, M. and Schild, G. C. (1982) Lancet 2 122–124

Minor, P. D., Schild, G. C., Wood, J. M. and Dandawate, C. N. (1980) J. gen Virol 51 157–170 1

Minor, P. D., Schild, G. C., Ferguson, M., Magrath, D. I. Yates, P. J. and Spitz, M. (1982) J. gen Virol 61 167–176

Schild, G. C., Wood, J. M., Minor, P. D., Dandawate, C. N. and Magrath, D. I. (1980) J. gen Virol 51 157–170

Schild, G. C. and Dowdle, W. R. (1975) Influenza virus characterization and diagnostic serology. In 'Influenza Viruses and Influenza' ed E. D. Kilbourne, Academic Press NY pages 6–368

Schild, G. C., Winters, W. D. & Brand, C. M. (1971) Bull. Wld. Hlth. Org 45 465–471

Schild G. C. (1972) J. gen Virol. 15 99–103.

Schild, G. C, Wood, J. M., Minor, P. D., Dandawate, C. N. and Magrath, D. I. (1981) Develop.biol. Standard. 47, 77–85 (S. Karger, Basel).

TABLE 1

| Type 3 Sabin Poliovirus | Type 1 Sabin Poliovirus | Type 1 Mahoney Poliovirus | Mutant Group 1 | Mutant Group 2 | Mutant Group 3 | Mutant Group 4 | Mutant Group 5 | Mutant Group 6 | Mutant Group 7 | Mutant Group 8 |
|---|---|---|---|---|---|---|---|---|---|---|
| Ala | | Thr | | | | | | | | |

TABLE 1-continued

| Type 3 Sabin Poliovirus | (cont.) | (cont.) | (cont.) | (cont.) | (cont.) | (cont.) | (cont.) | (cont.) | (cont.) | (cont.) | (cont.) |
|---|---|---|---|---|---|---|---|---|---|---|---|
| Ile |  | Thr |  |  |  |  |  |  |  |  |  |
| Ile |  | Met |  |  |  |  |  |  |  |  |  |
| Glu | Thr | Thr |  |  |  |  |  |  |  |  |  |
| Val |  |  |  |  |  |  |  |  |  |  |  |
| Asp |  |  |  |  |  |  |  |  |  |  |  |
| Asn |  |  |  |  |  |  |  |  |  |  |  |
| Glu | Ser | Pro |  |  |  |  |  |  |  |  |  |
| Gln | Ala | Ala |  |  |  |  |  |  |  |  |  |
| Pro | Ser | Ser |  |  |  |  |  |  |  |  |  |
| Thr |  |  | Ile | Ala |  |  |  |  |  |  |  |
| Thr | Lys |  |  |  | Asn |  |  |  |  |  | Ser |
| Arg | Asn | Asn |  |  |  | Gln |  |  |  |  |  |
| Ala | Lys | Lys |  |  |  |  |  |  |  | Thr |  |
| Gln | Asp | Asp |  |  |  |  |  | Leu | Pro |  |  |
| Lys |  |  |  |  |  |  |  |  |  |  |  |
| Leu |  |  |  |  |  |  |  |  |  |  |  |
| Phe |  |  |  |  |  |  |  |  |  |  |  |

| Type 3 Sabin Poliovirus | Mutant Group 9 | Mutant Group 11 | Mutant Group 12 | Mutant Group 13 | Mutant Group 14 | Mutant Group 15 | Mutant Group 16 | Mutant Group 17 | Mutant Group 18 | Mutant Group 19 | Mutant Group 20 | Mutant Group 21 | Mutant Group 22 |
|---|---|---|---|---|---|---|---|---|---|---|---|---|---|
| Ala |  |  |  |  |  |  |  |  |  |  |  |  |  |
| Ile |  |  |  |  |  |  |  |  |  |  |  |  |  |
| Ile |  |  |  |  |  |  |  |  |  |  |  |  |  |
| Glu |  |  |  |  |  |  |  |  |  |  |  |  |  |
| Val |  |  |  |  |  |  |  |  |  |  |  |  |  |
| Asp |  |  |  |  |  |  |  |  |  |  |  |  |  |
| Asn |  |  |  |  |  |  |  |  |  |  |  |  |  |
| Glu | Gly |  |  |  |  |  |  |  |  |  |  |  |  |
| Gln |  |  |  |  |  |  |  |  |  |  |  |  |  |
| Pro |  |  |  |  |  |  |  |  |  |  |  |  |  |
| Thr |  |  |  |  | Asn |  |  |  | Ser | Ile | Asn | Ile | Ile |
| Thr |  |  |  |  |  |  | Ile |  |  |  |  | Asn | Ala |
| Arg |  |  |  |  |  | Trp |  | Gly |  |  |  |  |  |
| Ala |  |  | Val |  |  |  |  |  | Thr | Thr | Thr | Thr | Thr |
| Gln |  |  |  | Arg | His |  |  |  |  |  |  |  |  |
| Lys |  |  |  |  |  |  |  |  |  |  |  |  |  |
| Leu |  |  |  |  |  |  |  |  |  |  |  |  |  |
| Phe |  |  |  |  |  |  |  |  |  |  |  |  |  |

TABLE 2

Reaction of neutralising monoclonal antibodies with antigenic mutants of type 3 poliovirus

| Mutant | 25-1-14 | 25-4-12 | 27-4-4 | 199 | 194 | 134 | 208 | 175 | 204 | 197 | 165 | Selecting monoclonal antibodies |
|---|---|---|---|---|---|---|---|---|---|---|---|---|
| 1 | r | r |  |  |  |  |  |  |  | r | r | 25-1-14,25-4-12,25-5-5,27-4-4 |
| 2 | r | r |  | r | r |  |  |  |  | r | r | 25-1-14,25-4-12,199,165,25-5-5 |
| 3 | r | r | r | r | r |  | r | r | r | r | r | 25-4-12,27-4-4,175,204,25-5-5 |
| 4 | r | r | r | r | r | r | r | r |  | r | r | 25-4-12,27-4-4,204,165,132 |
| 5 |  |  |  | r | r | r | r | r |  |  | r | 199,134,132,165,175,204 |
| 6 |  |  |  | r | r | r | r |  |  |  | r | 199,165,132 |
| 7 |  |  |  | r | r | r | r | r | r |  | r | 134,165 |
| 8 |  | r |  |  |  | r | r |  |  | r |  | 27-4-4 |
| 9 | r | r | r | r | r | r | r | r |  | r | r | 27-4-4,199,175,204 |
| 10 | r | r | r | r | r | r | r | r | r | r | r | 27-4-4,134,175 |
| 11 |  |  |  | r | r |  | r | r | r | r | r | 199,175,204,165 |
| 12 |  | r |  | r | r | r | r | r |  |  | r | 175 |
| 13 | r | r |  | r |  | r | r | r |  |  | r | 175,204 |
| 14 | r | r |  |  |  |  | r |  |  | r | r | 175 |
| 15 | r | r | r | r |  |  | r | r | r | r | r | 175,204 |
| 16 | r | r |  | r |  |  | r |  | r |  | r | 199,204,165 |

Reaction was assessed by neutralization of $5 \times 10^4$ TC1D50 units of virus by a 1/10 dilution of antibody ascitic fluid.
r = resistant. The wild type was neutralized by all antibodies.

TABLE 3

Point mutations and consequent amino acid substitutions in groups of mutant viruses derived from Leon type 3 poliovirus

|  | 1 | 2 | 3 | 4 | 5 | 6 | 7 | 8 | 9 | 10 | 11 | 12 |
|---|---|---|---|---|---|---|---|---|---|---|---|---|
| Type 1 (Mahoney) | GUG Val | GAU Asp | AAC Asn | CCA Pro | GCU Ala | UCG Ser | ACC Thr | ACG Thr | AAU Asn | AAG Lys | GAU Asp | AAG Lys |
| Type 3 (Leon) | GUG Val | GAC Asp | AAU Asn | GAA Glu | CAA Gln | CCA Pro | ACC Thr | ACC Thr | CGG Arg | GCA Ala | CAG Gln | AAA Lys |
| Mutant Group |  |  |  |  |  |  |  |  |  |  |  |  |
| 1 |  |  |  |  |  |  |  | AUC Ile |  |  |  |  |
| 2 |  |  |  |  |  |  |  | GCC |  |  |  |  |

TABLE 3-continued

Point mutations and consequent amino acid substitutions in groups of mutant viruses derived from Leon type 3 poliovirus

| | 1 | 2 | 3 | 4 | 5 | 6 | 7 | 8 | 9 | 10 | 11 | 12 |
|---|---|---|---|---|---|---|---|---|---|---|---|---|
| | | | | | | | Ala | | | | | |
| 3 | | | | | | | | AAC Asn | | | | |
| 4 | | | | | | | | | CAG Gln | | | |
| 5 | | | | | | | | | | | CUG Leu | |
| 6 | | | | | | | | | | | CCG Pro | |
| 7 | | | | | | | | | ACA Thr | | | |
| 8 | | | | | | | | UCC Ser | | | | |
| 9 | | | | GGA Gly | | | | | | | | |
| 10 | | | | | | | | | | | | |
| 11 | | | | | | | | | | GUA Val | | |
| 12 | | | | | | | | | | | CGG Arg | |
| 13 | | | | | | | | | | | CAC His | |
| 14 | | | | | | | AAC Asn | | | | | |
| 15 | | | | | | | | | UGG Trp | | | |
| 16 | | | | | | | | AUC Ile | | | | |

The amino acid recognition requirements of monoclonal antibody 25-1-14 for neutralization of mutant viruses

| | | Amino acids at position No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | Parental seq | Val | Asp | Asn | Glu | Gln | Pro | Thr | Thr | Arg | Ala | Gln | Lys |
| A | Gp5 | Val | Asp | Asn | Glu | Gln | Pro | Thr | Thr | Arg | Ala | Leu | Lys |
| | Gp6 | Val | Asp | Asn | Glu | Gln | Pro | Thr | Thr | Arg | Ala | Pro | Lys |
| | Gp7 | Val | Asp | Asn | Glu | Gln | Pro | Thr | Thr | Arg | Thr | Gln | Lys |
| | Gp8 | Val | Asp | Asn | Glu | Gln | Pro | Thr | Ser | Arg | Ala | Gln | Lys |
| | Gp11 | Val | Asp | Asn | Glu | Gln | Pro | Thr | Thr | Arg | Val | Gln | Lys |
| | Gp12 | Val | Asp | Asn | Glu | Gln | Pro | Thr | Thr | Arg | Ala | Arg | Lys |
| B | Gp1 | Val | Asp | Asn | Glu | Gln | Pro | Ile | Thr | Arg | Ala | Gln | Lys |
| | Gp2 | Val | Asp | Asn | Glu | Gln | Pro | Ala | Thr | Arg | Ala | Gln | Lys |
| | Gp3 | Val | Asp | Asn | Glu | Gln | Pro | Thr | Asn | Arg | Ala | Gln | Lys |
| | Gp4 | Val | Asp | Asn | Glu | Gln | Pro | Thr | Thr | Gln | Ala | Gln | Lys |
| | Gp9 | Val | Asp | Asn | Gly | Gln | Pro | Thr | Thr | Arg | Ala | Gln | Lys |
| | Gp13 | Val | Asp | Asn | Glu | Gln | Pro | Thr | Thr | Arg | Ala | His | Lys |
| | Gp14 | Val | Asp | Asn | Glu | Gln | Pro | Asn | Thr | Arg | Ala | Gln | Lys |
| | Gp15 | Val | Asp | Asn | Glu | Gln | Pro | Thr | Thr | Trp | Ala | Gln | Lys |
| | Gp16 | Val | Asp | Asn | Glu | Gln | Pro | Thr | Ile | Arg | Ala | Gln | Lys |

A Amino acid substitutions in the proposed antigenic site of type 3 poliovirus mutants derived from Leon which are neutralized by monoclonal antibody 25-1-14
B Amino acid substitutions in the antigenic site of mutant viruses which result in them not being neutralized by 25-1-14

TABLE 5

Summary of requirements for neutralization of mutant type 3 viruses by individual monoclonal antibodies in terms of amino acids at critical positions of the antigenic site

| | Position No. and parental amino acid sequence: | | | | | | | | | | | |
|---|---|---|---|---|---|---|---|---|---|---|---|---|
| Monoclonal antibody | 1 Val | 2 Asp | 3 Asn | 4 Glu | 5 Gln | 6 Pro | 7 Thr | 8 Thr | 9 Arg | 10 Ala | 11 Gln | 12 Lys |
| 25-1-14 | | | | + | | | + | +* | + | − | ? | |
| 25-4-12 | | | | + | | | + | +* | + | − | ? | |
| 27-4-4 | | | | + | | | − | ? | + | − | − | |
| 199 | | | | + | | | ? | +* | + | + | + | |
| 194 | | | | + | | | ? | +* | + | + | ? | |
| 134 | | | | + | | | − | ? | − | ? | + | |
| 208 | | | | + | | | − | + | ? | + | + | |
| 175 | | | | + | | | ? | ? | ? | + | ? | |
| 204 | | | | − | | | − | +* | + | ? | + | |
| 197 | | | | + | | | + | ? | + | ? | ? | |
| 165 | | | | + | | | ? | +* | + | + | + | |

TABLE 5-continued

Summary of requirements for neutralization of mutant type 3 viruses by individual monoclonal antibodies in terms of amino acids at critical positions of the antigenic site

| Monoclonal antibody | Position No. and parental amino acid sequence: | | | | | | | | | | | |
|---|---|---|---|---|---|---|---|---|---|---|---|---|
| | 1 Val | 2 Asp | 3 Asn | 4 Glu | 5 Gln | 6 Pro | 7 Thr | 8 Thr | 9 Arg | 10 Ala | 11 Gln | 12 Lys |
| Number of monoclonal antibodies requiring parental amino acid at the stated position | | | | 10 | | | 3 | 7 | 8 | 5 | 4 | |

*antibodies fail to react with viruses with any substitution other than a serine at this position
Blank no mutations detected at this site, that is these amino acids were conserved throughout
+ The monoclonal antibodies have an unambiguous requirement for parental amino acid at this position
− No positive requirement for the parental amino acid at this position
? Substitution of an amino acid at this position had an ambiguous effect on virus neutralization

TABLE 6

Antibody titres to peptide S10 in rabbits immunized with BTG coupled oligopeptides S10 or S10a

| Rabbit | Immunized with: | Serum sample | | | | |
|---|---|---|---|---|---|---|
| | | Day 0 | Day 14 | Day 27 | Day 55 | Day 62 |
| 52 | S10 | <100 | 800* | 3200 | 25000 | 25000 |
| 53 | S10 | <100 | 3200 | 12800 | 25000 | 25000 |
| 54 | S10 | <100 | 400 | 3200 | | |
| 55 | S10a | <100 | 800 | 3200 | | |
| 56 | S10a | <100 | 800 | 3200 | ND | ND |
| 57 | S10a | <100 | 800 | 3200 | 6400 | 25000 |

*reciprocal of final dilution showing

TABLE 7

Antibody titres to poliovirus 3 detected by antigen blocking tests in rabbits immunized with oligopeptides S10 and S10

| Rabbit | Oligopeptide used for immunization | Poliovirus type 3(D antigen) Day of serum sample | | | | | Poliovirus type 3(C antigen) Day of serum sample † | | | | | Poliovirus 1 + 2 D & C antigen | |
|---|---|---|---|---|---|---|---|---|---|---|---|---|---|
| | | 0 | 14 | 27 | 41 | 55 | 0 | 14 | 27 | 41 | 55 | 0 | 41 |
| 52 | S10 | — | — | — | — | — | — | — | 4 | 4 | 4 | — | — |
| 53 | S10 | — | — | 4* | 32 | 16 | — | — | 4 | 32 | 16 | — | — |
| 54 | S10 | — | — | 32 | 64 | 16 | — | — | 32 | 64 | 8 | — | — |
| 55 | S10a | — | — | 16 | 64 | 16 | — | — | 32 | 64 | 8 | — | — |
| 57 | S10a | — | — | 16 | 64 | 128 | — | 2 | 16 | 64 | 64 | — | — |

*reciprocal of highest serum dilution producing reduction in zone size
—indicated titres <1:2
†poliovirus P3/Leon/USA/37 strain

TABLE 8

Immunoprecipitin reactions with poliovirus type 1, 2, and 3 (D) antigen of sera from rabbits immunized with oligopeptides S10 and S10a

| Rabbit | Test antigen | Day of serum sample | | | | |
|---|---|---|---|---|---|---|
| | | 0 | 27 | 41 | 55 | 62 |
| 52 | P1 | — | — | — | — | — |
| | P2 | — | — | — | — | — |
| | P3 | — | — | + | ++ | +++ |
| 53 | P1 | — | — | — | — | — |
| | P2 | — | — | — | — | — |
| | P3 | — | + | ++ | ++ | ++ |
| 54 | P1 | — | — | — | — | — |
| | P2 | — | — | — | — | — |
| | P3 | — | — | + | ++ | +++ |
| 55 | P1 | — | — | — | — | — |
| | P2 | — | — | — | — | — |
| | P3 | — | + | ++ | +++ | +++ |
| 57 | P1 | — | — | — | — | — |
| | P2 | — | — | — | — | — |
| | P3 | — | + | +++ | +++ | +++ |

− no detectable precipitin reaction
+ weak precipitin line
++ precipitin line of moderate intensity
+++ strong precipitin line
P1 concentrates of poliovirus type 1/Mahoney/USA/41
P2 concentrates of poliovirus type 2/5148/UK/65
P3 concentrates of poliovirus type 3/Saukett/USA/50

TABLE 9

Immunoprecipitin reactions of rabbit sera with various strains of poliovirus type 3

| Poliovirus type 3 strains | Rabbit No. | | | | | |
|---|---|---|---|---|---|---|
| | 55 | | 57 | | 53 | |
| | (a) | (b) | (a) | (b) | (a) | (b) |
| P3/Leon/USA/1937 | — | +++ | — | +++ | — | ++ |
| P3/Sabin vaccine strain | — | ++ | — | ++ | — | ++ |
| P3/Saukett/USA/1950 | — | +++ | — | +++ | — | ++ |
| P3/30/Canada/52 | — | ++ | — | ++ | — | ++ |
| P3/77750/USA/54 | — | +++ | — | +++ | — | +++ |
| P3/119/Rumania/1970 | — | +++ | — | +++ | — | +++ |
| P1/Mahoney/USA/41 | — | — | — | — | — | — |
| P2/5148/UK/65 | — | — | — | — | — | — |

(a) sera collected at day 0
(b) sera collected at day 55

TABLE 10

Neutralizing antibody titres to poliovirus type 3 strains in rabbits following immunization with oligopeptides S10 and S10a

| Rabbit | Oligopeptide used for immunization | P3/Leon/USA/1937 virus Day of serum sample | | | | | P3/Saukett/USA/1950 virus Day of serum sample | | | | |
|---|---|---|---|---|---|---|---|---|---|---|---|
| | | 0 | 27 | 41 | 55 | 62 | 0 | 27 | 41 | 55 | 62 |
| 53 | S10 | — | — | — | 16 | 8 | — | | | 8 | 8 |

TABLE 10-continued

Neutralizing antibody titres to poliovirus type 3 strains in rabbits following immunization with oligopeptides S10 and S10a

| Rabbit | Oligopeptide used for immunization | P3/Leon/USA/1937 virus Day of serum sample | | | | | P3/Saukett/USA/1950 virus Day of serum sample | | | | |
|---|---|---|---|---|---|---|---|---|---|---|---|
| | | 0 | 27 | 41 | 55 | 62 | 0 | 27 | 41 | 55 | 62 |
| 54 | S10 | — | — | | 3 | 3 | 4 | — | | | ND | 6 |
| 55 | S10a | — | — | — | 23 | 23 | — | | | 32 | 45 |
| 57 | S10a | — | — | 2 | 8 | 8 | — | | | 10 | 10 |

—indicates neutralization titres <1:2

TABLE 11

Neutralising antibody titres to P3/Leon/USA/37 in guinea pigs primed with oligopeptide S1

| Guinea Pig | Immunized with | Virus neutralization titres one week after boost with 1D antigen unit P3/Leon/37 |
|---|---|---|
| 2R | oligopeptide S1-BTG | 200 |
| 2Y | " | 15,000 |
| 2P | " | 600 |
| 7R | " | 15,000 |
| 7Y | " | 17,000 |
| 7B | " | 24,000 |
| 7G | " | 20,000 |
| 20G | BTG only | 20 |
| 20R | " | 200 |
| 20Y | " | 200 |

We claim:

1. A synthetic polypeptide, suitable for use in vaccination against or diagnosis of a disease caused by an enterovirus, which is a hexapeptide coded for by codons 93 to 98 in the RNA sequence coding for the structural capsid protein VP1 of a poliovirus type 3 Sabin strain or by equivalent codons of another enterovirus or is an antigenic equivalent of such a hexapeptide, the antigenic equivalent being:
   (i) a said hexapeptide modified by the inclusion therein of one or more changes to the amino acid sequence or
   (ii) a longer peptide of up to eighteen amino acid residues incorporating a said hexapeptide or a said modified hexapeptide sequence, each said antigenic equivalent being capable of raising antibodies capable of neutralising the same strain and type of enterovirus as the said hexapeptide to which each said antigenic equivalent corresponds and the numbers of the codons being counted from the 5'-terminus of the nucleotide sequence coding for the VP1 capsid protein.

2. The polypeptide of claim 1 which is a said longer peptide coded for by a continuous run of rom seven to eighteen codons in the RNA sequence coding for the VP1 capsid protein of a poliovirus type 3 Sabin strain, which run includes codons 93 to 98 and starts with a codon numbered no lower than 86 and ends with a codon numbered no higher than 103, or by equivalent codons of another enterovirus.

3. The polypeptide of claim 1, suitable for use in vaccination against or diagnosis of a disease caused by type 1 poliovirus, which is a hexapeptide having the formula (IIa):

$$\text{H-A}_o\text{-A}_1\text{-A}_2\text{-A}_3\text{-A}_4\text{A}_5\text{-OH} \quad \text{(II a)}$$

in which $A_1$ is Ala, $A_2$ is Ser, $A_3$ is Thr, $A_5$ is Asn and either (A) $A_o$ is Ser and $A_4$ is Lys or (B) $A_o$ is Pro and $A_4$ is Thr.

4. The polypeptide of claim 1, suitable for use in vaccination against or diagnosis of a disease caused by type 1 poliovirus, which is a said modified hexapeptide (i) wherein a hexapeptide having the formula (IIa):

$$\text{H-A}_0\text{-A}_1\text{-A}_2\text{-A}_3\text{-A}_4\text{-A}_5\text{-OH} \quad \text{(II a)}$$

in which $A_1$ is Ala, $A_2$ is Ser, $A_3$ is Thr, $A_5$ is Asn and either (A) $A_o$ is Ser and $A_4$ is Lys or (B) $A_o$ is Pro and $A_4$ is Thr, has been modified by the inclusion of one or more said changes to the amino acid sequence.

5. The polypeptide of claim 1, suitable for use in vaccination against or diagnosis of a disease caused by type 1 poliovirus, which is a said longer peptide (ii) incorporating the amino acid sequence of a hexapeptide having the formula (IIa):

$$\text{H-A}_o\text{-A}_1\text{-A}_2\text{-A}_3\text{-A}_4\text{-A}_5\text{-OH} \quad \text{(IIa)}$$

in which $A_1$ is Ala, $A_2$ is Ser, $A_3$ is Thr, $A_5$ is Asn and either (A) $A_o$ is Ser and $A_4$ is Lys or (B) $A_o$ is Pro and $A_4$ is Thr.

6. The polypeptide of claim 1, suitable for use in vaccination against or diagnosis of a disease caused by type 3 poliovirus, having the formula (IIb):

$$\text{H-A}'_o\text{-A}'_1\text{-A}'_2\text{-A}'_3\text{-A}'_4\text{-A}'_5\text{-OH} \quad \text{(IIb)}$$

in which (A) $A'_o$ is Glu, $A'_1$ is Gln, $A'_2$ is Pro, $A'_3$ is Thr, $A'_4$ is Thr and $A'_5$ is Arg, or (B), with the others of $A'_o$ to $A'_5$ being defined in (A), (a) $A'_3$ is Ile or (b) $A'_4$ is Ser or (c) $A'_5$ is Gln.

7. The polypeptide of claim 1, suitable for use in vaccination against or diagnosis of a disease caused by type 3 poliovirus, having the formula (IIc):

$$\text{H-A}''_o\text{-A}''_1\text{-A}''_2\text{-A}''_3\text{-A}''_4\text{-A}''_5\text{-OH} \quad \text{(IIc)}$$

in which (A) $A''_o$ is Gly, $A''_1$ is Gln, $A''_2$ is Pro, $A''_3$ is Thr, $A''_4$ is Thr and $A''_5$ is Arg, or (B), with the others of $A''_o$ to $A''_5$ being defined in (A), (B) (a) $A''_o$ is Glu and $A''_3$ is Ser, Ala or Asn, or (b) $A''_o$ is Glu and $A''_4$ is Asn or Ile, or (c) $A''_o$ is Glu and $A''_5$ is Trp or Gly, or (d) $A''_o$ is Glu, $A''_3$ is Ile and $A''_4$ is Ala or Asn.

8. The polypeptide of claim 1, suitable for use in vaccination against or diagnosis of a disease caused by type 3 poliovirus, which is a said modified hexapeptide (i) wherein the hexapeptide having the formula (IId):

$$\text{H-A}'''_o\text{-A}'''_1\text{-A}'''_2\text{-A}'''_3\text{-A}'''_4\text{-A}'''_5\text{-OH} \quad \text{(IId)}$$

in which (A) $A'''_o$ is Glu, $A'''_1$ is Gln, $A'''_2$ is Pro, $A'''_3$ is Thr, $A'''_4$ is Thr and $A'''_5$ is Arg or (B), with the others of $A'''_o$ to $A'''_5$ being as defined in (A), (a) $A'''_o$ is Gly or (b) $A'''_3$ is Ile, Ser, Ala or Asn or (c) $A'''_4$ is Asn, Ser or Ile or (d) $A'''_5$ is Gln, Trp or Gly or (e) $A'''_3$ is Ile and $A'''_4$ is Asn or Ala, has been modified by the inclusion therein of one or more said changes to the amino acid sequence.

9. The polypeptide of claim 1, suitable for use in vaccination against or diagnosis of a disease caused by type 3 poliovirus, which is a said longer peptide (ii) incorporating the amino acid sequence of the hexapeptide having the formula (IId):

$$H\text{-}A'''_o\text{-}A'''_1\text{-}A'''_2\text{-}A'''_3\text{-}A'''_4\text{-}A'''_5\text{-}OH \qquad (IId)$$

in which (A) $A'''_o$ is Glu, $A'''_1$ is Gln, $A'''_2$ is Pro, $A'''_3$ is Thr, $A'''_4$ is Thr and $A'''_5$ is Arg or (B), with the others of $A'''_o$ to $A'''_5$ being as defined in (A), (a) $A'''_o$ is Gly or (b) $A'''_3$ is Ile, Ser, Ala or Asn or (c) $A'''_4$ is Asn, Ser or Ile or (d) $A'''_5$ is Gln, Trp or Gly or (e) $A'''_3$ is Ile and $A'''_4$ is Asn or Ala.

10. The polypeptide of claim 2 which is coded for by codons 86 to 103 in the RNA sequence coding for the VP1 capsid protein of a poliovirus type 3 Sabin strain or by equivalent codons of another enterorvirus.

11. The polypeptide of claim 2, suitable for use in vaccination against or diagnosis of a disease caused by type 3 poliovirus, having the formula;
H-Ala-Ile-Ile-Glu-Val-Asp-Asn-$A'_o$-$A'_1$-$A'_2$-$A'_3$-$A'_4$-$A'_5$Ala-Gln-Lys-Leu-Phe-OH
in which (A) $A'_o$ is Glu, $A'_1$ is Gln, $A'_2$ is Pro, $A'_3$ is Thr, $A'_4$ is Thr and $A'_5$ is Arg, or (B), with the others of $A'_o$ to $A'_5$ being defined in (A), (a) $A'_3$ is Ile or (b) $A'_4$ is Ser or (c) $A'_5$ is Gln.

12. The polypeptide of claim 2, suitable for use in vaccination against or diagnosis of a disease caused by type 3 poliovirus, having the formula:
H-Ala-Ile-Ile-Glu-Val-Asp-Asn-$A''_o$-$A''_1$-$A''_2$-$A''_3$-$A''_4$-$A''_5$-Ala-Gln-Lys-Leu-Phe-OH
in which (A) $A''_o$ is Gly, $A''_1$ is Gln, $A''_2$ is Pro, $A''_3$ is Thr, $A''_4$ is Thr and $A''_5$ is Arg, or (B), with the others of $A''_o$ to $A''_5$ being defined in (A), (B) (a) $A''_o$ is Glu and $A''_3$ is Ser, Ala or Asn, or (b) $A''_o$ is Glu and $A''_4$ is Asn or Ile, or (c) $A''_o$ is Glu and $A''_5$ is Trp or Gly, or (d) $A''_o$ is Glu, $A''_3$ is Ile and $A''_4$ is Ala or Asn.

13. The polypeptide of claim 2, suitable for use in vaccination against or diagnosis of a disease caused by type 1 poliovirus, having the formula:
H-$A_{-7}$-$A_{-6}$-$A_{-5}$-Thr-Val-Asp-Asn-$A_o$-Ala-Ser-Thr-$A_4$-Asn-Lys-Asp-Lys-Leu-Phe-OH
in which (A) $A_{-7}$ is Ala, $A_{-6}$ is Ile, $A_{-5}$ is Ile, $A_o$ is Ser and $A_4$ is Lys, or (B) $A_{-7}$ is Thr, $A_{-6}$ is Thr, $A_{-5}$ is Met, $A_o$ is Pro and $A_4$ is Thr.

14. A synthetic polypeptide, suitable for use in vaccination against or diagnosis of a disease caused by an enterovirus, which is an octapeptide coded for by codons 93 to 100 in the RNA sequence coding for the structural capsid protein VP1 of a poliovirus type 3 Sabin strain or by equivalent codons of another enterovirus or is an antigenic equivalent of such an octapeptide, the antigenic equivalent being:
(i') a said octapeptide modified by the inclusion therein of one or more changes to the amino acid sequence or
(ii') a longer peptide of up to eighteen amino acid residues incorporating a said octapeptide or a said modified octapeptide sequence, each said antigenic equivalent being capable of raising antibodies capable of neutralising the same strain and type of enterovirus as the said octapeptide to which each said antigenic equivalent corresponds and the numbers of the codons being counted from the 5'-terminus of the nucleotide sequence coding for the VP1 capsid protein.

15. The polypeptide of claim 14, suitable for use in vaccination against or diagnosis of a disease caused by type 1 poliovirus, which is an octapeptide having the formula (Ia):

$$H\text{-}A_o\text{-}A_1\text{-}A_2\text{-}A_3\text{-}A_4\text{-}A_5\text{-}A_6\text{-}A_7\text{-}OH \qquad (Ia)$$

in which $A_1$ is Ala, $A_2$ is Ser, $A_3$ is Thr, $A_5$ is Asn, $A_6$ is Lys, $A_7$ is Asp and either (A) $A_o$ is Ser and $A_4$ is Lys or (B) $A_o$ is Pro and $A_4$ is Thr.

16. The polypeptide of claim 14, suitable for use in vaccination against or diagnosis of a disease caused by type 1 poliovirus, which is a said modified octapeptide (i') wherein an octapeptide having the formula (Ia):

$$H\text{-}A_o\text{-}A_1\text{-}A_2\text{-}A_3\text{-}A_4\text{-}A_5\text{-}A_6\text{-}A_7\text{-}OH \qquad (Ia)$$

in which $A_1$ is Ala, $A_2$ is Ser, $A_3$ is Thr, $A_5$ is Asn, $A_6$ is Lys, $A_7$ is Asp and either (A) $A_o$ is Ser and $A_4$ is Lys or (B) $A_o$ is Pro and $A_4$ is Thr, has been modified by the inclusion therein of one or more said changes to the amino acid sequence.

17. The polypeptide of claim 14, suitable for use in vaccination against or diagnosis of a disease caused by type 1 poliovirus, which is a said longer peptide (ii') incorporating the amino acid sequence of an octapeptide having the formula (Ia):

$$H\text{-}A_o\text{-}A_1\text{-}A_2\text{-}A_3\text{-}A_4\text{-}A_5\text{-}A_6\text{-}A_7\text{-}OH \qquad (Ia)$$

in which $A_1$ is Ala, $A_2$ is Ser, $A_3$ is Thr, $A_5$ is Asn, $A_6$ is Lys, $A_7$ is Asp and either (A) $A_o$ is Ser and $A_4$ is Lys or (B) $A_o$ is Pro and $A_4$ is Thr.

18. The polypeptide of claim 14, suitable for use in vaccination against or diagnosis of a disease caused by type 3 poliovirus, which is the octapeptide having the formula (Ib):

$$H\text{-}A^I_o\text{-}A^I_1\text{-}A^I_2\text{-}A^I_3\text{-}A^I_4\text{-}A^I_5\text{-}A^I_6\text{-}A^I_7\text{-}OH \qquad (Ib)$$

in which (A) $A^I_o$ is Glu, $A^I_1$ is Gln, $A^I_2$ is Pro, $A^I_3$ is Thr, $A^I_4$ is Thr, $A^I_5$ is Arg, $A^I_6$ is Ala and $A^I_7$ is Gln, or (B), with the others of $A^I_o$ to $A^I_7$ being as defined in (A),
(a) $A^I_o$ is Gly, or
(b) $A^I_3$ is Ile, Ala or Asn, or
(c) $A^I_4$ is Asn, Ser or Ile, or
(d) $A^I_5$ is Gln or Trp, or
(e) $A^I_6$ is Thr or Val, or
(f) $A^I_7$ is Leu, Pro, Arg or His.

19. The polypeptide of claim 14, suitable for use in vaccination against or diagnosis of a disease caused by type 3 poliovirus, which is the octapeptide having the formula (Ic):

$$H\text{-}A^{II}_o\text{-}A^{II}_1\text{-}A^{II}_2\text{-}A^{II}_3\text{-}A^{II}_4\text{-}A^{II}_5\text{-}A^{II}_6\text{-}A^{II}_7\text{-}OH \qquad (Ic)$$

in which (A) $A^{II}_o$ is Glu, $A^{II}_1$ is Gln, $A^{II}_2$ is Pro, $A^{II}_3$ is Thr, $A^{II}_4$ Thr, $A^{II}_5$ is Gly, $A^{II}_6$ is Ala and $A^{II}_7$ is Gln or (B), with the others of $A^{II}_o$ to $A^{II}_7$ being as defined in (A), (a) $A^{II}_3$ is Ser, Ile or Asn, $A^{II}_5$ is Arg and $A^{II}_6$ is Thr or (b) $A^{II}_3$ is Ile, $A^{II}_4$ is Asn or Ala, $A^{II}_5$ is Arg and $A^{II}_6$ is Thr.

20. The polypeptide of claim 14, suitable for use in vaccination against or diagnosis of a disease caused by type 3 poliovirus, which is a said modified octapeptide (i') wherein the octapeptide having the formula (Id):

$$\text{H-A}^{III}_0\text{-A}^{III}_1\text{-A}^{III}_2\text{-A}^{III}_3\text{-A}^{III}_4\text{-A}^{III}_5\text{-A}^{III}_6\text{-A}^{III}_7\text{-OH} \quad \text{(Id)}$$

which (A) $A^{III}_0$ is Glu, $A^{III}_1$ is Gln, $A^{III}_2$ is Pro, $A^{III}_3$ is Thr, $A^{III}_4$ is Thr, $A^{III}_5$ is Arg, $A^{III}_6$ is Ala and $A^{III}_7$ is Gln, or (B), with the others of $A^{III}_0$ to $A^{III}_7$ being as defined in (A), (a) $A^{III}_0$ is Gly
(b) $A^{III}_3$ is Ile, Ala or Asn, or
(c) $A^{III}_4$ is Asn, Ser or Ile, or
(d) $A^{III}_5$ is Gln or Trp, or
(e) $A^{III}_6$ is Thr or Val, or
(f) $A^{III}_7$ is Leu, Pro, Arg or His, or
(g) $A^{III}_5$ is Gly, or
(h) $A^{III}_3$ is Ser, Ile or Asn and $A^{III}_6$ is Thr,
(i) $A^{III}_3$ is Ile, $A^{III}_4$ is Asn or Ala and $A^{III}_6$ is Thr, has been modified by the inclusion of one or more said changes to the amino acid sequence.

21. The polypeptide of claim 14, suitable for use in vaccination against or diagnosis of a disease caused by type 3 poliovirus, which is a said longer peptide (ii') incorporating the amino acid sequence of the octapeptide having the formula (Id):

$$\text{H-A}^{III}_0\text{-A}^{III}_1\text{-A}^{III}_2\text{-A}^{III}_3\text{-A}^{III}_4\text{-A}^{III}_5\text{-A}^{III}_6\text{-A}^{III}_7\text{-OH} \quad \text{(Id)}$$

which (A) $A^{III}_0$ is Glu, $A^{III}_1$ is Gln, $A^{III}_2$ is Pro, $A^{III}_3$ is Thr, $A^{III}_4$ is Thr, $A^{III}_5$ is Arg, $A^{III}_6$ is Ala and $A^{III}_7$ is Gln, or (B), with the others of $A^{III}_0$ to $A^{III}_7$ being as defined in (A), (a) $A^{III}_0$ is Gly
(b) $A^{III}_3$ is Ile, Ala or Asn, or
(c) $A^{III}_4$ is Asn, Ser or Ile, or
(d) $A^{III}_5$ is Gln or Trp, or
(e) $A^{III}_6$ is Thr or Val, or
(f) $A^{III}_7$ is Leu, Pro, Arg or His, or
(g) $A^{III}_5$ is Gly, or
(h) $A^{III}_3$ is Ser, Ile or Asn and $A^{III}_6$ is Thr,
(i) $A^{III}_3$ is Ile, $A^{III}_4$ is Asn or Ala and $A^{III}_6$ is Thr.

22. The polypeptide of claim 5, wherein the said longer peptide (ii) is a polypeptide of formula (IIa) with a Cys residue attached at either terminus.

23. The polypeptide of claim 9, wherein the said longer peptide (ii) is a polypeptide of formula (IId) with a Cys residue attached at either terminus.

24. The polypeptide of claim 17, wherein the said longer peptide (ii') is a polypeptide of formula (Ia) with a Cys residue attached at either terminus.

25. The polypeptide of claim 21, wherein the said longer peptide (ii') is a polypeptide of formula (Id) with a Cys residue attached at either terminus.

26. The polypeptide of claim 5, wherein the said longer peptide (ii) comprises repeats of the polypeptide of formula (IIa).

27. The polypeptide of claim 9, wherein the said longer peptide (ii) comprises repeats of the polypeptide of formula (IId).

28. The polypeptide of claim 17, wherein the said longer peptide (ii') comprises repeats of the polypeptide of formula (Ia).

29. The polypeptide of claim 21, wherein the said longer peptide (ii') comprises repeats of the polypeptide of formula (Id).

* * * * *